United States Patent
Koussa et al.

(10) Patent No.: US 10,876,177 B2
(45) Date of Patent: Dec. 29, 2020

(54) COMPOSITIONS AND METHODS RELATING TO NUCLEIC ACID-PROTEIN COMPLEXES

(71) Applicants: President and Fellows of Harvard College, Cambridge, MA (US); Children's Medical Center Corporation, Boston, MA (US)

(72) Inventors: Mounir Ahmad Koussa, Somerville, MA (US); Wesley Philip Wong, Cambridge, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 659 days.

(21) Appl. No.: 14/903,463

(22) PCT Filed: Jul. 10, 2014

(86) PCT No.: PCT/US2014/046251
§ 371 (c)(1),
(2) Date: Jan. 7, 2016

(87) PCT Pub. No.: WO2015/006626
PCT Pub. Date: Jan. 15, 2015

(65) Prior Publication Data
US 2016/0279257 A1    Sep. 29, 2016

Related U.S. Application Data

(60) Provisional application No. 61/844,818, filed on Jul. 10, 2013.

(51) Int. Cl.
| | | |
|---|---|---|
| C07K 1/107 | (2006.01) | |
| C07K 7/06 | (2006.01) | |
| A61K 47/65 | (2017.01) | |
| C12N 9/96 | (2006.01) | |

(52) U.S. Cl.
CPC ...... *C12Y 304/22044* (2013.01); *A61K 47/65* (2017.08); *C07K 1/1077* (2013.01); *C07K 7/06* (2013.01); *C12N 9/96* (2013.01)

(58) Field of Classification Search
None
See application file for complete search history.

(56) References Cited

U.S. PATENT DOCUMENTS

| | | |
|---|---|---|
| 2009/0088372 A1 | 4/2009 | Roy et al. |
| 2011/0321183 A1 | 12/2011 | Ploegh et al. |
| 2012/0282670 A1 | 11/2012 | Rossomando |

FOREIGN PATENT DOCUMENTS

| | | | |
|---|---|---|---|
| JP | 2010-536341 A | 12/2010 | |
| WO | WO 2009/023270 A2 | 2/2009 | |
| WO | WO 2012/142659 | * 10/2012 | |
| WO | WO-2012142659 A1 | * 10/2012 | ............. C07K 14/00 |
| WO | WO 2013/003555 A1 | 1/2013 | |
| WO | WO 2013/067489 A1 | 5/2013 | |

OTHER PUBLICATIONS

Lu et al. (Chemical Strategies for the Synthesis of Peptide-Oligonucleotide Conjugates, Bioconjugate Chem. 2010, 21, 187-202).*
Tropea et al. (A Generic Method for the Production of Recombinant Proteins in *Escherichia coli* Using a Dual Hexahistidine-Maltose-Binding Protein Affinity Tag, Macromolecular Crystallography Protocols pp. 1-19, 2007).*
Lee et al. (Nature Nanotechnology, vol. 7, published on Jun. 3, 2012).*
EP 14822570.9, dated Jan. 24, 2017, Extended European Search Report.
PCT/US2014/046251, dated Nov. 4, 2014, International Search Report and Written Opinion.
PCT/US2014/046251, dated Jan. 21, 2016, International Preliminary Report on Patentability.
JP 2016-525792, dated Jun. 19, 2018, Notice of Reasons for Rejection.
Extended European Search Report dated Jan. 24, 2017 for Application No. EP 14822570.9.
Japanese Office Action dated Jun. 19, 2018 for Application No. JP 2016-525792.
International Search Report and Written Opinion dated Nov. 4, 2014 for Application No. PCT/US2014/046251.
International Preliminary Report on Patentability dated Jan. 21, 2016 for Application No. PCT/US2014/046251.
Cecconi et al., Protein-Dna chimeras for single molecule mechanical folding studies with the optical tweezers. Eur Biophys J. Jul. 2008;37(6):729-38. doi: 10.1007/s00249-007-0247-y. Epub Jan. 9, 2008.
Chandrasekaran et al., Programmable DNA nanoswitches for detection of nucleic acid sequences. ACS Sens. 2016;1:120-3.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

Provided are methods and compositions relating to conjugation of nucleic acids and proteins of interest under conditions that maintain protein activity. The nucleic acid-protein conjugates may be used in nucleic acid nanostructures such as those generated using DNA origami methods.

13 Claims, 8 Drawing Sheets
Specification includes a Sequence Listing.

(56) References Cited

OTHER PUBLICATIONS

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.

Dietz et al., Folding DNA into twisted and curved nanoscale shapes. Science. Aug. 7, 2009;325(5941):725-30.

Douglas et al., A logic-gated nanorobot for targeted transport of molecular payloads. Nature. Feb. 17, 2012;335:831-4.

Douglas et al., Self-assembly of DNA into nanoscale three-dimensional shapes. Nature. May 21, 2009;459(7245):414-8. 11 pages.

Gordon et al., Reactivity of biarylazacyclooctynones in copper-free click chemistry. J Am Chem Soc. Jun. 6, 2012;134(22):9199-208. doi: 10.1021/ja3000936. Epub May 24, 2012.

Guimares et al., Site-specific C-terminal and internal loop labeling of proteins using sortase-mediated reactions. Nat Protoc. Sep. 2013;8(9):1787-99. doi: 10.1038/nprot.2013.101. Epub Aug. 29, 2013. 21 pages.

Halvorsen et al., Nanoengineering a single-molecule mechanical switch using DNA self-assembly. Nanotechnology. Dec. 9, 2011;22(49):494005(1-8). doi: 10.1088/0957-4484/22/49/494005. Epub Nov. 21, 2011.

Han et al., DNA origami with complex curvatures in three-dimensional space. Science. Apr. 15, 2011;332(6027):342-6. doi: 10.1126/science.1202998.

Hansen et al., Nanoswitch-linked immunosorbent assay (NLISA) for fast, sensitive, and specific protein detection. PNAS. Sep. 26, 2017;114(39):10367-10372. Supporting Information, 4 pages.

Kazmierczak et al., Cadherin 23 and protocadherin 15 interact to form tip-link filaments in sensory hair cells. Nature. Sep. 6, 2007;449(7158):87-91.

Kitayama et al., Chemistry and Living Organism. 2012;50(6):414-22. Japanese.

Koussa, A novel and robust technique for creating protein-DNA hybrids. LMW-Harvard Young Scientists' Forum. From Molecules to Organisms V. Munich, Germany. Jul. 8-12, 2013. Corresponding oral presentation occurred on Jul. 11, 2013. Abstract, 2 pages.

Koussa et al., Protocol for sortase-mediated construction of DNA-protein hybrids and functional nanostructures. Methods. 2014; 67:134-41. Epub Feb. 22, 2014.

Koussa et al., DNA nanoswitches: A quantitative platform for gel-based biomolecular interaction analysis. Nat Methods. Feb. 2015;12(2):123-6. 8 pages.

Le et al., Probing nucleosome stability with a dna origami nanocaliper. ACS Nano. Jul. 26, 2016;10(7):7073-84. doi: 10.1021/acsnano. 6b03218. Epub Jul. 6, 2016. 29 pages.

Levary et al., Protein-protein fusion catalyzed by sortase A. PLoS One. Apr. 6, 2011;6(4):e18342. doi: 10.1371/journal.pone.0018342. 6 pages.

Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.

Linko et al., The enabled state of DNA nanotechnology. Curr Opin Biotechnol. Aug. 2013;24(4):555-61. doi: 10.1016/j.copbio.2013. 02.001. Epub Apr. 6, 2013.

Niemeyer, The developments of semisynthetic DNA-protein conjugates. Trends Biotechnol. Sep. 2002;20(9):395-401.

Popp et al., Sortagging: a versatile method for protein labeling. Nat Chem Biol. Nov. 2007;3(11):707-8. Epub Sep. 23, 2007.

Pritz et al., Synthesis of biologically active peptide nucleic acid-peptide conjugates by sortase-mediated ligation. J Org Chem. May 11, 2007;72(10):3909-12. Epub Apr. 14, 2007.

Rothemund, Folding DNA to create nanoscale shapes and patterns. Nature. Mar. 16, 2006;440(7082):297-302.

Saccà et al., Functionalization of DNA nanostructures with proteins. Chem Soc Rev. Dec. 2011;40(12):5910-21. doi: 10.1039/c1cs15212b. Epub Oct. 5, 2011.

Schaeffer et al., Synthesis and applications of covalent protein-DNA conjugates. Australian J Chem: Int J for Chem Sci. Jan. 1, 2009;62(10):1328-1332.

Sotomayor et al., Structure of a force-conveying cadherin bond essential for inner-ear mechanotransduction. Nature. Dec. 6, 2012;492(7427):128-32. doi: 10.1038/nature11590. Epub Nov. 7, 2012. 7 pages.

Sotomayor et al., Structural determinants of cadherin-23 function in hearing and deafness. Neuron. Apr. 15, 2010;66(1):85-100. doi: 10.1016/j.neuron.2010.03.028.

Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013. 13 pages.

Tsukiji et al., Sortase-mediated ligation: A gift from Gram-positive bacteria to protein engineering. Chembiochem. Mar. 23, 2009;10(5):787-98. doi: 10.1002/cbic.200800724.

Witte et al., Production of unnaturally linked chimeric proteins using a combination of sortase-catalyzed transpeptidation and click chemistry. Nat Protoc. Sep. 2013;8(9):1808-19. doi: 10.1038/nprot. 2013.103. Epub Aug. 29, 2013. 16 pages.

Yang et al., Nanostructures as programmable biomolecular scaffolds. Bioconjug Chem. Aug. 19, 2015;26(8):1381-95. doi:10.1021/acs.bioconjchem.5b00194. Epub May 22, 2015.

Zhang et al., Structural DNA nanotechnology: State of the art and future perspective. J Am Chem Soc. Aug. 13, 2014;136(32):11198-211. doi:10.1021/ja505101a. Epub Jul. 28, 2014.

\* cited by examiner

COMPOSITIONS AND METHODS RELATING TO NUCLEIC ACID-PROTEIN COMPLEXES

RELATED APPLICATIONS

This application is a national stage filing under 35 U.S.C. § 371 of International Application No. PCT/US2014/046251, filed Jul. 10, 2014, which was published under PCT Article 21(2) in English, and which claims the benefit of U.S. Provisional Application No. 61/844,818 filed Jul. 10, 2013, and entitled "COMPOSITIONS AND METHODS RELATING TO NUCLEIC ACID-PROTEIN COMPLEXES", the entire contents of each of which are incorporated by reference herein.

FEDERALLY SPONSORED RESEARCH

This invention was made with U.S. Government support under DC002281 awarded by the National Institutes of Health. The U.S. Government has certain rights in the invention.

BACKGROUND OF INVENTION

DNA has become the scaffold of choice for the construction of self-assembling nanostructures. As techniques for the programmed patterning of these structures have advanced, it is now possible to create complex assemblies (Linko and Dietz, Curr. Opin. Biotechnol. 24:555-561, 2013). To take these structural elements and make them into a functional nanomachine one often needs to incorporate proteins at very specific sites (Niemeyer, Trends in Biotech 20:395-401, 2002). The barrier is coming up with a successful means of coupling a protein of interest to DNA. Chemistries routinely used for linking proteins to oligonucleotides (oligos) include di-sulfide linkages and thiol-primary-amine linkages (Cecconi C. et al., Eur. Biophys. J. 37(6):729-38, 2008); Halvorsen et al., Nanotechnol. 22:494005-494012, 2011; Niemeyer and Sacca, Chem. Soc. Rev. 40: 5910-5921, 2011). Although these chemistries are sometimes effective, they react with functional groups common in biology. These techniques can thus not be used when the protein of interest has endogenous cysteines or when one wants to attach to a specific primary amine (in addition to the N-terminus each lysine provides a primary amine). To overcome many of these issues groups have worked on developing bio-orthogonal techniques such as copper-free click-chemistry (Gordon et al., J. Am. Chem. Soc. 134: 9199-9208, 2012). Although these techniques overcome the issue of specificity and stoichiometry, they suffer from an issue facing all three techniques. All of these techniques require reactions to be carried out at suboptimal physiological conditions. Be it long periods at room temperature, oxidizing/reducing conditions, or high/low pH conditions, these chemistries begin to fail when working with many proteins which are not very thermo stable and have a tendency to aggregate and/or precipitate out of solution under these conditions. In addition to these obstacles with these chemistries conditions have to be varied meticulously from protein to protein and there is no means of selectively purifying out the desired product.

SUMMARY OF INVENTION

This disclosure provides, in part, novel and robust methods for conjugating nucleic acids to proteins that overcome the shortcomings of the prior art techniques. These methods frontload the chemistry to be performed on nucleic acids, including oligonucleotides, and small, typically synthetic, peptides. Such nucleic acids and peptides are typically more tolerant of non-physiological conditions that may be used to perform certain chemistries contemplated in this disclosure.

This disclosure provides a two-step method, and variations thereof, that involves first conjugating a nucleic acid (e.g., a DNA) to a short, typically synthetic peptide, to form a nucleic acid-peptide conjugate, and then conjugating the nucleic acid-peptide conjugate to a protein of interest using a transpeptidase (e.g., a sortase enzyme) reaction. At least one advantage of the two-step approach is the ability to spare the protein from unfavorable reaction environments that might compromise the activity of the protein. With the two-step approach, these unfavorable reaction conditions are used in the first step, and the protein is introduced in the second step.

Thus, the methods of the disclosure, in some instances, involve conjugating a nucleic acid, such as an oligonucleotide, to an amino acid sequence comprising one or more contiguous N-terminal glycine (G) residues. In some embodiments, the amino acid sequence comprises three contiguous N-terminal glycine residues. The amino acid sequence is typically comprised in a short peptide, typically a synthetic peptide. The N-terminal GGG motif is recognized by the sortase enzyme used in the methods of this disclosure.

The amino acid sequence may further comprise additional amino acid sequence that may be used for purification purposes. These amino acid sequences may be referred to herein as purification tags or affinity labels, and include but are not limited to His-tags and Flag sequences (or Flag tags), the amino acid sequences of which are known in the art and are provided herein.

Conjugation of the oligonucleotide to the peptide may be accomplished using for example a bio-orthogonal copper catalyzed click chemistry reaction. The oligonucleotide to be conjugated to the peptide may comprise an azide. The azide may be located on a 3' end or a 5' end or it may be an internal azide. The peptide to be conjugated may comprise an alkyne, which acts as the complimentary click reagent. Alternatively, the peptide may comprise the azide and the oligonucleotide may comprise the alkyne. It is to be understood that other conjugation methods may be used to effect conjugation of the nucleic acid to the peptide. For example, this first step may also be accomplished using Sulfosuccinimidyl-4-(N-maleimidomethyl) cyclohexane-1-carboxylate (SMCC) to couple a cystine (in a peptide) to an amine-functionalized oligonucleotide.

The resultant product of this first reaction step is a nucleic acid (e.g., the oligonucleotide) conjugated to an amino acid sequence (i.e., the peptide) comprising one or more (e.g., three) glycine residues, and optionally a purification tag such as but not limited to a Flag amino acid sequence. The nucleic acids coupled to the peptides may be removed (e.g., separated from other reactants) and optionally purified from the reaction mixture by taking advantage of the purification tag. One approach is the use of beads such as magnetic beads, or a column-based bead slurry, either of which comprises a binding partner for the purification tag that binds to the purification tag (e.g., the binding partner may be an antibody specific for the purification tag).

The amino acid sequence may further contain an additional cleavable sequence. Such sequence may be cleaved in the presence of an enzyme or by another mechanism. In this way, once the conjugated nucleic acid is separated from other reactants, the purification tag may be removed from the conjugated nucleic acid, leaving only the terminal one or more (e.g., three) glycine residues that are then accessible to the sortase enzyme used in the second step. In some embodiments, the enzyme cleavable amino acid sequence is cleavable by Tobacco Etch Virus (TEV) protease. An example of an amino acid sequence that is cleavable by TEV protease is an amino acid sequence comprising ENLYFQ (SEQ ID NO: 1). Alternatively, the cleavable sequence may be cleaved through a non-enzymatic process, such as light. The cleavable sequence is typically located between the purification tag and the one or more (e.g., three) glycine residues.

In the second step of the method, the resultant nucleic acid conjugated to one or more (e.g., three) terminal glycine residues is then reacted with a protein of interest. The protein of interest may naturally contain an amino acid sequence that is also a target sequence for the sortase enzyme or another transpeptidase, or alternatively the protein may be engineered to contain such an amino acid sequence. These amino acid sequences may be referred to herein as sortase (or transpeptidase) target sequences.

One example of a sortase target sequence is LPXTGX'$_n$, where X and X' are independently selected amino acids and n is any number or any range of numbers greater than zero, including for example 1-90, 1-99, or 1-100 (SEQ ID NO: 2). X'$_n$ therefore intends that the amino acid sequence may contain any number of amino acid residues at one end (i.e., n number of X' amino acid residues, wherein each X' amino acid residue is independently selected from every other X' amino acid residue, wherein n may be 1-100, or 1-99 or 1-90, or any number therebetween). One such sequence is LPETGX'$_n$, wherein X' is an amino acid and n is any number or any range of numbers greater than zero, including for example 1-90, 1-99, or 1-100 (SEQ ID NO: 3). The terms "amino acids" and "amino acid residues" are used interchangeably herein. It is also to be understood that X and X' may be any amino acids in any of the embodiments described herein. As described herein, the sortase target sequence may further comprise a purification tag.

The reaction between the protein of interest and the oligonucleotide-peptide conjugate occurs in the presence of a sortase enzyme or another transpeptidase. In some embodiments, the sortase is sortase A. In some embodiments, the sortase is an evolved variant of sortase A, such as that described by Chen et al., PNAS 108:11399-11404, 2011. The terms "sortase" and "sortase enzyme" are used interchangeably herein. The sortase enzyme performs a transposition of a glycine residue conjugated to the nucleic acid (via the conjugated peptide) and a glycine residue in the sortase target sequence present in or conjugated to the protein of interest.

The product of this second reaction is the nucleic acid conjugated to the protein of interest through the amino acid linker. The amino acid linker may have a sequence of LPXTG$_n$, wherein n denotes the number of G residues and is any number or any range of numbers greater than zero (SEQ ID NO: 17). In some embodiments, the amino acid linker may have a sequence of LPXTGGG (SEQ ID NO: 9). In some embodiments, the amino acid linker may have a sequence of LPETG$_n$, wherein n denotes the number of G residues and is any number or any range of numbers greater than zero (SEQ ID NO: 4). In some embodiments, the linker has the sequence of LPETGGG (SEQ ID NO: 5).

This final conjugated product can then be purified using, for example, beads or other affinity based processes. Such purification may entail separating the nucleic acid-protein conjugate from other reaction components such as the sortase enzyme, the TEV enzyme, and/or any amino acid sequence released from the protein following the sortase-mediated transposition. This case be accomplished through the differential use or presence of purification tags following the sortase-mediated action. As an example, the reaction components such as the sortase enzyme, the TEV protease and/or the amino acid sequence liberated from the protein of interest following sortase-mediated transposition may be conjugated to a purification tag, and this tag may be used to remove these components away from the final conjugated product of interest. In a preferred embodiment, all components to be removed, for example from the final product, are conjugated to the same purification tag. Suitable purification tags include a His-tag (e.g., 6 His residues, (SEQ ID NO: 6)) or the Flag amino acid sequence comprising or consisting of DYKDDDDK (SEQ ID NO: 7). Such purification steps are useful to render a nucleic acid-protein conjugate/complex of interest free of any side products and reactants.

Thus, in one aspect, the disclosure provides a method comprising reacting (1) a nucleic acid (e.g., a DNA) conjugated to an amino acid sequence comprising one or more N-terminal glycine (G) residues with (2) a protein comprising a C-terminal amino acid sequence of LPXTGX'n, where X and X' are any independently selected amino acids and n is any number ranging from 1-99 (SEQ ID NO: 8), in the presence of a sortase enzyme, to form a complex comprising the nucleic acid covalently conjugated to the protein through an amino acid linker having an amino acid sequence of LPXTGGG, where X is any amino acid (SEQ ID NO: 9). The linker and the nucleic acid may be present at or near the C-terminal of the protein of interest post-conjugation.

In another aspect, the disclosure provides a method comprising reacting (1) a nucleic acid (e.g., a DNA) conjugated to an amino acid sequence comprising a terminal glycine (G) residue and (or with) (2) a protein comprising a terminal amino acid sequence of LPETGX$_n$, wherein X is an amino acid and n is a number greater than 0 or a range of numbers greater than 0 (SEQ ID NO: 10), in the presence of a sortase enzyme, to form a complex comprising the nucleic acid covalently conjugated to the protein through an amino acid linker having an amino acid sequence of LPETGGG (SEQ ID NO: 5). In some embodiments, "n" may be 1-99 amino acids in length. In some embodiments, "n" is a number greater than 1.

In some embodiments, the sortase enzyme and the protein comprising a terminal, such as a C-terminal, amino acid sequence of LPETGX$_n$ (SEQ ID NO: 10) each comprises a His-tag. In the case of the protein of interest, the His tag may be provided in, or as part of, the X$_n$ (or X'$_n$) amino acid sequence of the sortase target sequence.

In some embodiments, the nucleic acid conjugated to an amino acid sequence comprising a terminal glycine (G) residue is formed by a bio-orthogonal copper catalyzed click chemistry reaction between a nucleic acid and a peptide comprising one or more, and preferably three, G residues. In some embodiments, the bio-orthogonal copper catalyzed click chemistry reaction forms a conjugate (which may be referred to herein as a nucleic acid intermediate) comprising a nucleic acid conjugated to an amino acid sequence comprising one or more glycine (G) residues, and optionally a purification tag such as but not limited to a Flag sequence, and further optionally a cleavable amino acid sequence such as but not limited to a TEV target (cleavage) sequence, preferably located between the G residues and the purification tag.

The method may therefore further comprise cleaving the purification tag from the nucleic acid intermediate in order to render the glycine residues accessible to the sortase enzyme. As an example, in some embodiments, the method further comprises reacting the nucleic acid intermediate with TEV protease. In some embodiments, the TEV protease is conjugated to a His-tag. The His-tag may be an amino acid sequence comprising or consisting of six histidine residues (SEQ ID NO: 6).

In another aspect, the invention provides a complex comprising a nucleic acid covalently conjugated to a protein through an amino acid linker having an amino acid sequence of LPETGGG (amino to carboxy) or GGGTEPL (carboxy to amino) (SEQ ID NO: 5). The placement of this linker between the nucleic acid and the protein of interest are illustrated in the Figures.

In some embodiments, the protein is a naturally occurring protein and the sortase target sequence or the linker sequence, such as LPXTGX'$_n$ (SEQ ID NO: 2) as defined above or LPETGGG (SEQ ID NO: 5), is not present in the naturally occurring protein.

In some embodiments, the nucleic acid is 1-100 nucleotides in length. In some embodiments, the nucleic acid comprises or consists of DNA prior to conjugation to the peptide.

In another aspect, the invention provides a composition comprising any of the foregoing complexes or conjugates in isolated form, whether such complexes or conjugates are intermediates or final products. Thus, the disclosure provides one or more conjugates each comprising a nucleic acid conjugated to a peptide, wherein the peptide comprises one or more (e.g., three) glycines. These conjugates may differ from each other with respect to their nucleic acid sequences but may have identical amino acid sequences. The disclosure similarly provides one or more distinct proteins each comprising a sortase target sequence such as LPXTGX'$_n$ (SEQ ID NO: 2) as defined above. The disclosure similarly provides a plurality of the foregoing nucleic acid-peptide conjugates and proteins for use in the preparation of nucleic acid-protein complexes or conjugates. The disclosure further provides one or more conjugates each comprising a nucleic acid conjugated to a protein through an amino acid linker having an amino acid sequence of LPXTGGG (SEQ ID NO: 9). These conjugates may differ from each other with respect to their nucleic acid sequences and/or their amino acid sequences. Thus, they may have identical nucleic acid sequences, or they may have identical amino acid sequences, or they may have different nucleic acid and amino acid sequences. Thus, the disclosure provides a plurality of any of the foregoing complexes, each in isolated form or the plurality in isolated form, optionally in the form of a library.

In another aspect, the invention provides a composition comprising any combination of two or more of the following: a nucleic acid conjugated to an amino acid sequence comprising a terminal glycine (G) residue (including three G residues), a protein comprising a terminal amino acid sequence of LPXTGX'$_n$, where X and X' are independently selected amino acids and n is any number or any range of numbers greater than zero, including for example 1-90, 1-99, or 1-100 (SEQ ID NO: 2), a sortase enzyme, and a TEV protease.

In another aspect, the invention provides a composition comprising any combination of two or more of the following: a nucleic acid conjugated to an amino acid sequence comprising a terminal glycine (G) residue (including three G residues), a protein comprising a terminal amino acid sequence of LPETGX'$_n$, wherein X' is an amino acid and n is a number greater than 0 or a range of numbers greater than 0, preferably 1-99 (SEQ ID NO: 10), a sortase enzyme, and a TEV protease. In some embodiments, n is a number greater than 1.

In some embodiments, any one or any combination of the protein, the sortase enzyme and the TEV protease is conjugated to a purification tag such as but not limited to a His-tag. In some embodiments, the His-tag is comprised in the X$_n$ (or X'$_n$) amino acid sequence of the sortase target sequence of or conjugated to the protein. In some embodiments, the composition further comprises beads that bind specifically to His-tags (anti-His beads).

In some embodiments, n is any number or any range of numbers from 1 to 100, or from 1 to 99, or from 1 to 90. In some embodiments, the His-tag is an amino acid sequence of six histidine residues (SEQ ID NO: 6).

The nucleic acid-protein complexes or conjugates may then be used with or incorporated into nucleic acid nanostructures such as but not limited to DNA origami nanostructures. This may be accomplished by hybridizing the nucleic acid portion of the conjugate to a nucleic acid nanostructure, including to a scaffold strain in a DNA origami structure. Alternatively, the nucleic acid-peptide intermediate may be incorporated into a nucleic acid nanostructure and the protein may be conjugated after the nucleic acid nanostructure is formed.

In some instances, the specific activity of the nucleic acid-protein complexes or conjugates formed according to the methods provided herein are at least 75%, at least 85%, at least 95%, or about 100% of the specific activity of the protein in an unconjugated and unmanipulated form. Thus, the conjugation methods provided herein do not significantly impact the activity of the proteins being manipulated.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

DETAILED DESCRIPTION OF INVENTION

Figure 1:
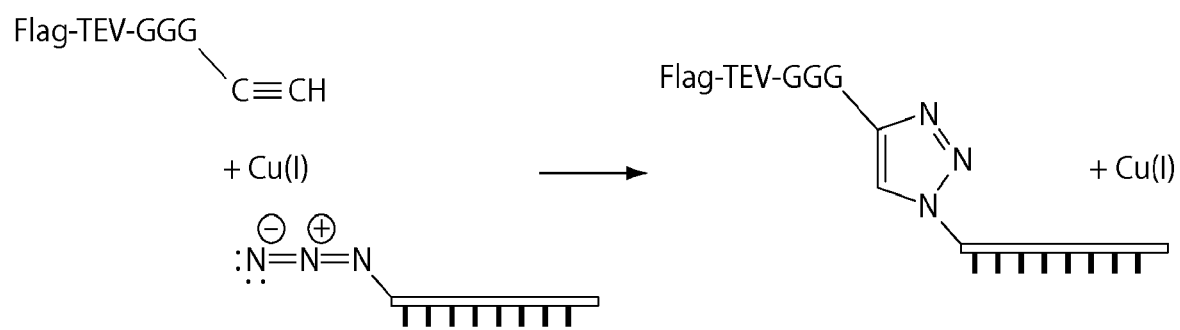
FIG. 1. Click chemistry to create Tri-glycine (GGG) oligonucleotide precursor. A custom peptide (DYKDDDD-KENLYFQGGG-Pra, SEQ ID NO: 12) is linked to a synthesized oligonucleotide with an azide modification through copper (I) catalyzed click chemistry.

The present disclosure provides compositions and methods relating to nucleic acid-protein complexes (also referred to herein interchangeably as nucleic acid-protein conjugates or oligonucleotide-protein conjugates). The disclosure provides methods of synthesis of such complexes, methods of use of such complexes, and compositions of the complexes themselves, as well as compositions comprising intermediates, including intermediate complexes or conjugates, in the synthesis process.

The synthesis methods provided herein are suited to conjugation of nucleic acids such as oligonucleotides to proteins of interest. Such protein-conjugated nucleic acids may then be used in nanotechnology applications such as but not limited to addressable nanostructures.

Disclosed herein is a general sortase-based protocol for covalently coupling proteins to DNA with minimal disturbance to protein function. A two-step process is used to accomplish this goal. First, a small synthetic peptide is bio-orthogonally and covalently coupled to a DNA oligonucleotide using click chemistry. Next, the DNA-peptide chimera is covalently linked to a protein of interest under protein-compatible conditions using the enzyme sortase. The protocol allows for the simple coupling and purification of a functional DNA-protein hybrid.

As an exemplary application, this technique was used to form an oligonucleotide bearing cadherin-23 and an oligonucleotide linked to protocadherin-15. Upon incorporation into a linear M13 scaffold (via for example DNA origami techniques), protein-DNA hybrids such as this exemplary hybrid serve as the gate to a binary nanoswitch, as described in greater detail herein.

The disclosed protocol is reliable and modular, facilitating the construction of libraries of functionalized oligonucleotides (i.e., oligonucleotides minimally coupled to one or more (e.g., 3) contiguous glycines) and proteins (i.e., proteins comprising sortase target sequences) that can be combined to form functional DNA-protein conjugates and in some instances nanostructures. These structures will enable a new class of functional nanostructures, which could be used for therapeutic and industrial processes.

The disclosed protocol therefore various challenges of prior art methods. In order to preserve protein function, protein-DNA coupling is performed under physiological conditions. In the disclosed two-step process, a small synthetic peptide is first coupled to a DNA oligonucleotide. Next, utilizing a sortase enzyme (Chen et al., PNAS 108: 11399-11404, 2011; Popp et al., Nat Chem Biol 3: 707-708, 2007), a protein of choice is coupled to the DNA-peptide chimera under physiological conditions. This strategy front-loads all of the protein-incompatible chemistry so that it is performed on an oligonucleotide and a synthetic peptide, which are far more tolerant of non-physiological conditions.

Sortase covalently links the N-terminus of one protein to a location near the C-terminus of another protein. Sortase recognizes an N-terminal GGG and a C-terminal LPXTGX'n, where X and X' can be any independently selected amino acid, and n can be any number of amino acids, including for example 1-99 (SEQ ID NO: 2). Sortase then facilitates the transposition of the glycine residues in the two proteins resulting in a covalent linkage between the two proteins and the release of GX'n.

The use of sortase can also be used to facilitate purification, as coupling of the oligonucleotide may be accompanied by the removal of an affinity tag. The protocol, detailed below, allows for the use of commercially available purification resins to yield the product of choice free of any side products and reactants. This technique can be used to generate libraries of oligonucleotides and proteins such that any proteins in the library can be easily and reliably attached anywhere along a DNA origami scaffold such as an M13 nucleic acid.

The disclosure contemplates use of sortase technology to generate DNA-protein hybrids for self-assembled nanostructures. To demonstrate the utility of this technique, a simple DNA-protein nanomachine in the form of a binary DNA-nanoswitch (Halvorsen et al., Nanotechnology 22:494005-494012, 2011), gated by the interacting pair of proteins cadherin-23 (CDH23) and protocadherin-15 (PCDH15) (Kazmierczak et al., Nature 449:87-91, 2007; Sotomayor et al., Nature 492:128-132, 2012). This self-assembled mechanical switch changes state to report the formation or rupture of biomolecular bonds (e.g., the switch is closed when CDH23 is bound to PCDH15 and open otherwise). CDH23 is covalently linked to an oligonucleotide which hybridizes one-third of the way in from one edge of the DNA scaffold (M13), and PCDH15 is linked to an oligonucleotide which hybridizes one-third of the way in from the other edge of the scaffold (FIG. 7). The result is a nanoswitch that has an end-to-end length of 3 μm when the proteins are not interacting, and an end-to-end length of 2 μm when the proteins are interacting. These two states are resolvable via gel electrophoresis as described by Halvorsen et al., Nanotechnology 22:494005-494012, 2011.

The synthesis methods are described below.

Figure 2:
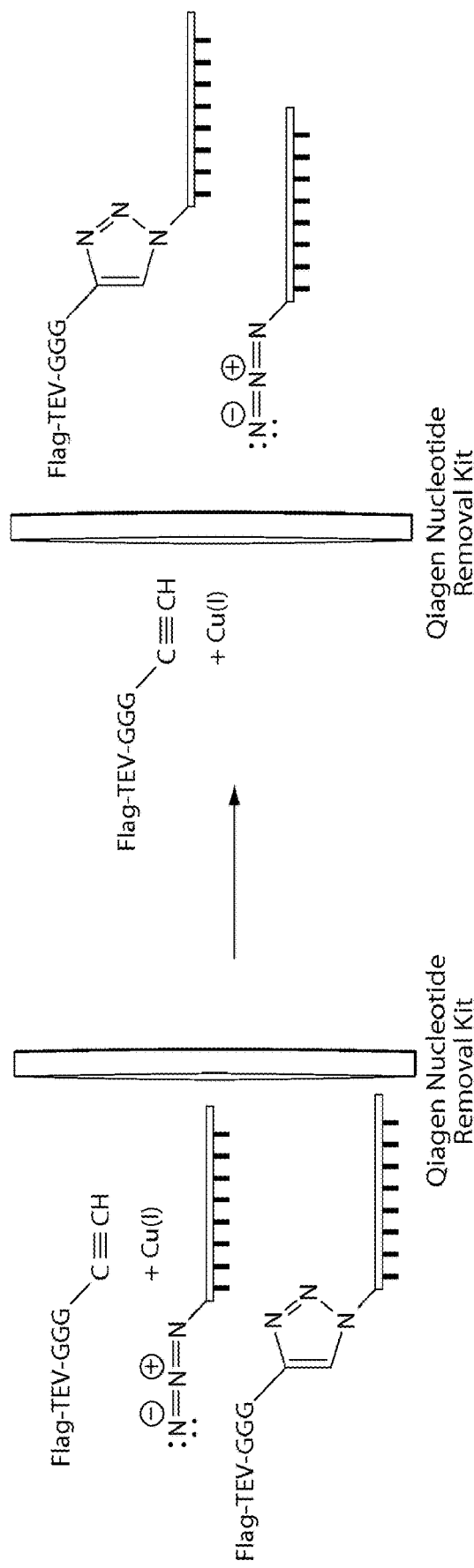
FIG. 2. Qiagen PCR cleanup kit used to remove catalytic Cu(I) and excess uncoupled peptide. Running the reaction product through a Qiagen kit allows for the isolation of the coupled and uncoupled oligo. As provided in the Figure, the coupled oligonucleotide can then be separated from the uncoupled oligonucleotide by virtue of its purification tag. Excess peptide and copper will remain on the membrane and/or be removed in the wash steps.
Figure 3:
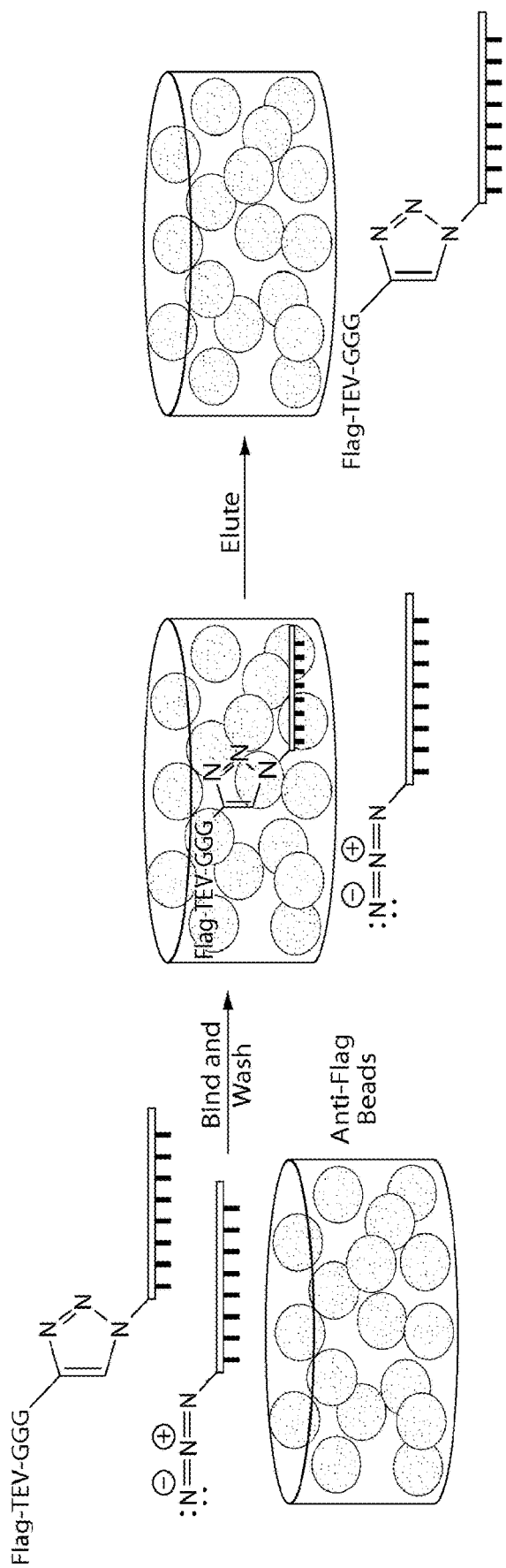
FIG. 3. Removal of uncoupled oligonucleotide through the purification tag. Binding the product of the Qiagen nucleotide removal kit to commercially available anti-Flag beads removes uncoupled oligonucleotide, leaving only the desired Tri-glycine oligonucleotide precursor (or oligonucleotide-peptide conjugate). Elution with Flag peptide releases the oligonucleotide from the affinity matrix.

In a first step, the synthetic oligonucleotide is linked to a small synthetic peptide (both of which are commercially available). In one example, the conjugation occurs using a bio-orthogonal copper (I) catalyzed click chemistry reaction (FIG. 1). The catalytic copper and excess reagents then can be removed using, for example, a commercially available kit and purification resin (FIGS. 2 and 3).

Figure 4:
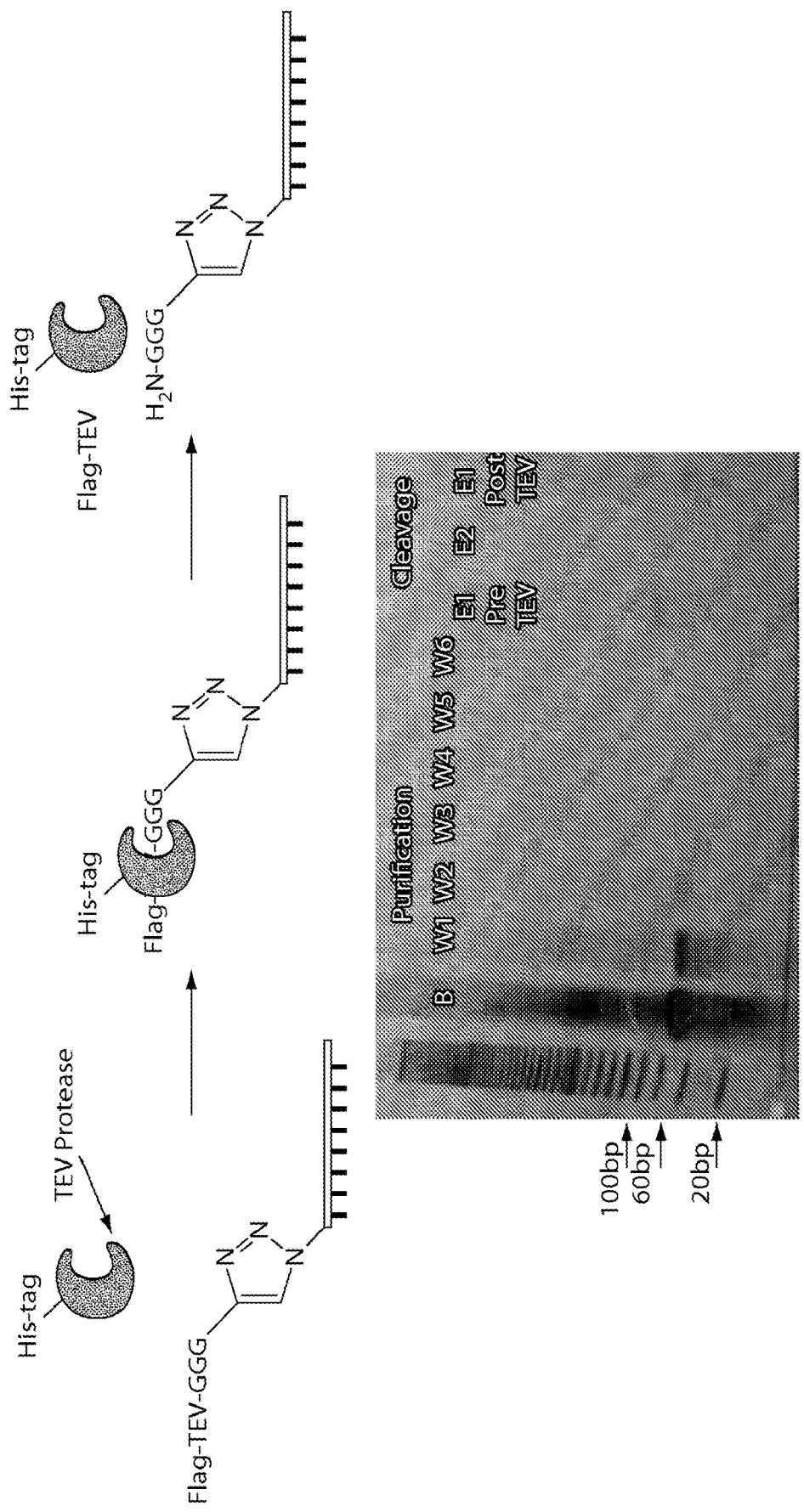
FIG. 4. TEV cleavage and polyacrylamide gel illustrating effectiveness of removal of excess, uncoupled oligonucleotide and efficiency of TEV cleavage. The TEV protease (crescent shape) can be applied to cleave the Flag purification tag, resulting in an oligonucleotide with a sortase-compatible GGG-peptide. The lanes of the gel are as follows: B is supernatant after binding to anti-Flag beads; W1-W6 are washes 1 through 6; E1 and E2 are elutions 1 and 2; and the left-most lane is a Bio-Rad 20 bp Molecular Ruler. Pre- and post-TEV refer to before and after TEV cleavage, respectively.

A region of the small synthetic peptide may be used for purification purposes. If it is present, it may then be removed through an enzymatic or non-enzymatic cleavage reaction. As illustrated in FIG. 4, in one example, the peptide sequence comprises a purification tag, an enzyme cleavable sequence, and GGG sequence. Incubation with a protease that targets the cleavable sequence such as a protease isolated from the Tobacco Etch Virus (TEV) yields an oligonucleotide covalently attached to a tri-glycine amino acid sequence.

Figure 5:
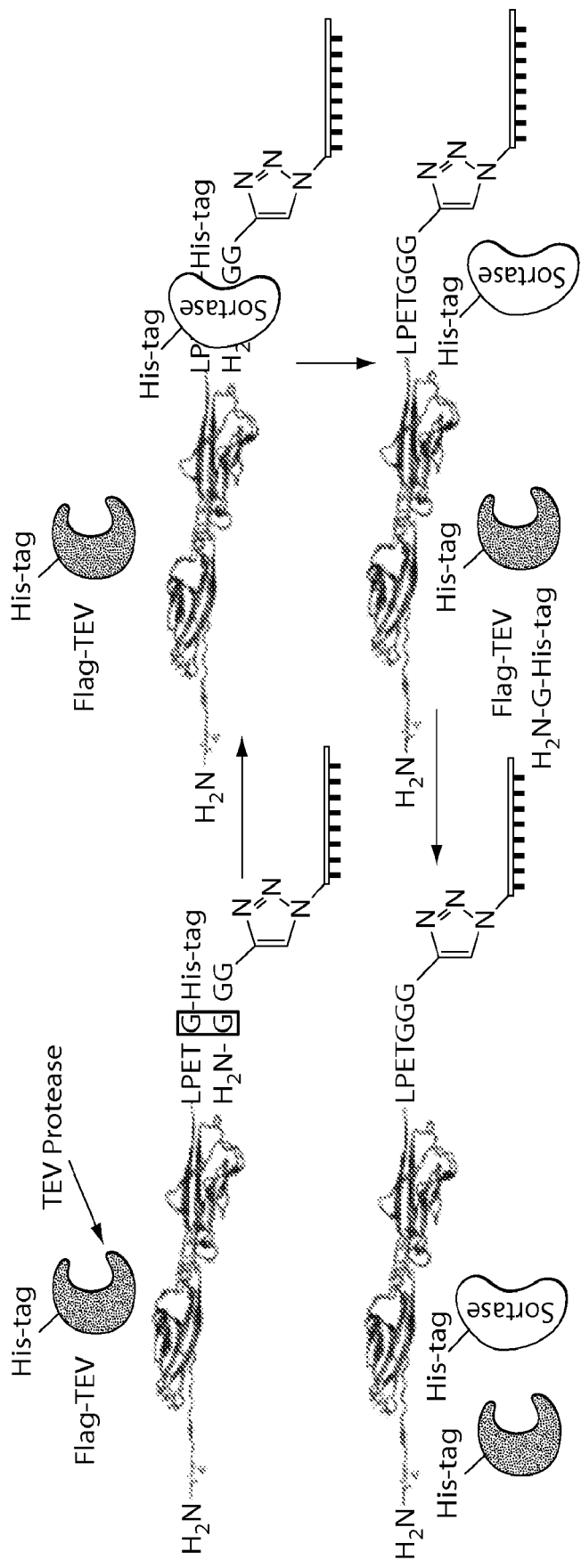
FIG. 5. Sortase-catalyzed production of protein-DNA hybrids. Sortase coupling scheme illustrating the transposition of the two glycine residues indicated by the rectangle. An LPETG-containing protein (LPETG is SEQ ID NO: 4), in this case CDH23 EC1+2, is coupled to the Gly-Gly-Gly-oligonucleotide via sortase. Sortase transposes the two glycine residues highlighted by the rectangle, resulting in the formation of a peptide bond between the protein and the Gly-Gly-Gly-oligo. Sortase binds to the $LPX_1TGX_2$ (SEQ ID NO: 2) sequence first. In this case, the sequence after the C-terminal-most glycine on the protein was a His-tag (SEQ ID NO: 6). The resultant conjugate comprises an LPETGGG linker (SEQ ID NO: 5).

This oligo-peptide hybrid (or complex) can then be covalently linked to any protein which has a C-terminal $LPXTGX'_n$, amino acid sequence, such as an $LPETGX'_n$ amino acid sequence, where X and X' represent any independently selected amino acids, and n is a number greater than zero such that $X'_n$ represents one or more amino acids, including but not limited to for example any number of amino acids in the range of 1-90 (SEQ ID NO: 2 and SEQ ID NO:3, respectively). In the presence of a sortase enzyme, the two glycine residues indicated with the rectangle in FIG. 5 (one of which is in the peptide sequence attached to the protein of interest and one of which is in the peptide attached to the oligonucleotide) are transposed resulting in a covalent linkage of the oligonucleotide and the protein, and cleavage of a glycine-X' peptide.

Figure 6:
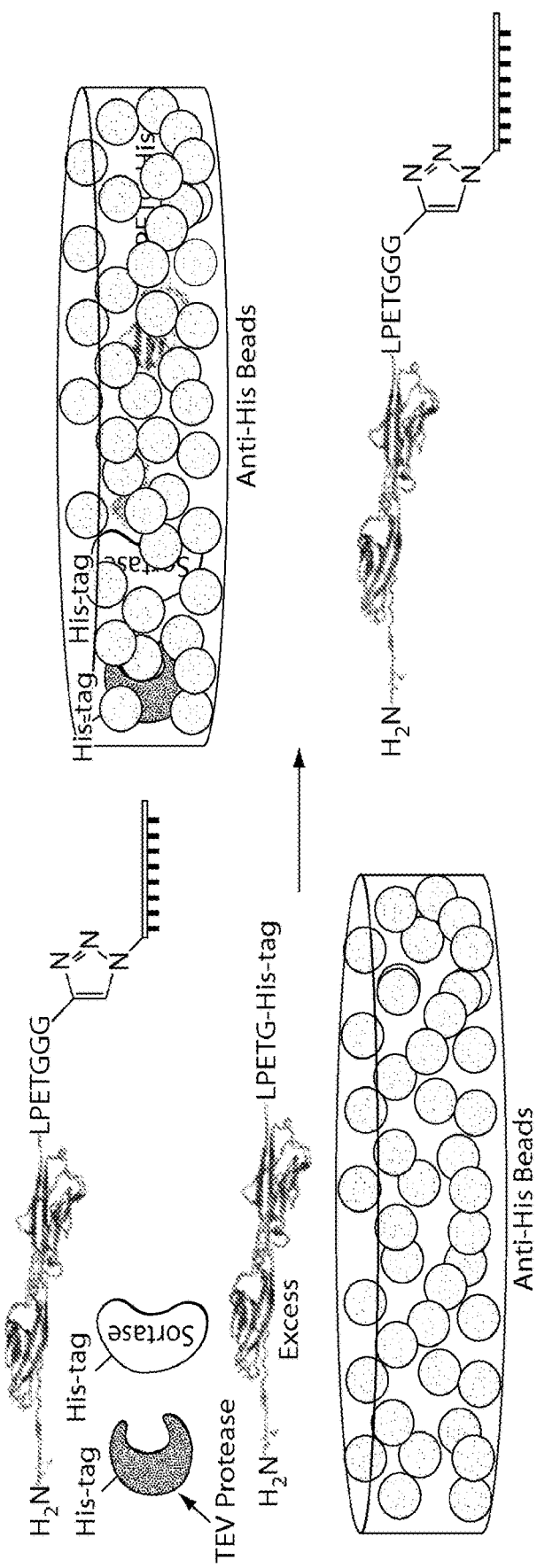
FIG. 6. Removal of reactants and catalysts. Upon completion of the coupling of the nucleic acid to the protein of interest, the final conjugate is present along with the TEV protease, the sortase enzyme, and excess unreacted protein of interest. In this example, all reactants contain the same purification tag (i.e., a His-tag), and thus they can be captured using anti-His beads and removed leaving only the final desired nucleic acid-protein conjugate product in the supernatant. The sortase selectively cleaves the His-tag off the final product as part of the transposition reaction. LPETG is SEQ ID NO: 4; LPETGGG is SEQ ID NO: 5.
Figure 7A:
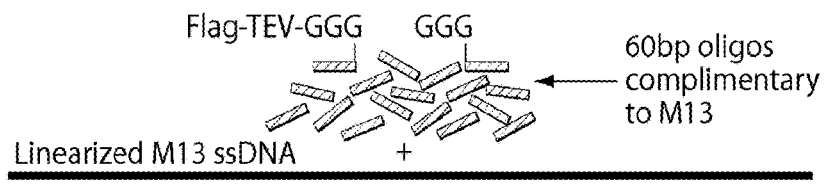
FIGS. 7A-F. A method for the formation of the binary DNA-nanoswitch. Linearized M13 single-stranded DNA (solid bottom line in each panel), complimentary oligonucleotides (shorter lines located adjacent to the solid line), CDH23 EC1+2 (introduced in panel C), and PCDH15 EC1+2 (introduced in panel E). (A to B) Annealing of functionalized and non-functionalized oligonucleotides to the M13 ssDNA scaffold. (B to C) Sortase is used to link a CDH23 fragment that contains LPETG (SEQ ID NO: 4) (see section 2.4.4 herein) to the Gly-Gly-Gly-modified oligonucleotide. The other oligonucleotide is protected by having the N-terminus blocked by a Flag-TEV sequence (see section 2.1 herein). (C to D) After successful coupling, the TEV protease is used to deprotect the second Gly-Gly-Gly-oligo, thereby priming it for sortase coupling (see section 2.4.4e herein). (D to E) sortase is then used again to attach a PCDH15 fragment containing LPETG (SEQ ID NO: 4) (see section 2.4.4k herein). (E to F, and vice versa) Upon binding of CDH23 to PCDH15, the DNA-nanoswitch is closed. Thermo-stable proteins can also be attached to a DNA origami scaffold by for example performing the sortase-based coupling reactions on the individual oligonucleotides separately prior to thermally annealing the oligos to the M13 scaffold, thus obviating the need for the protecting Flag-tag (2.3).
Figure 7B:
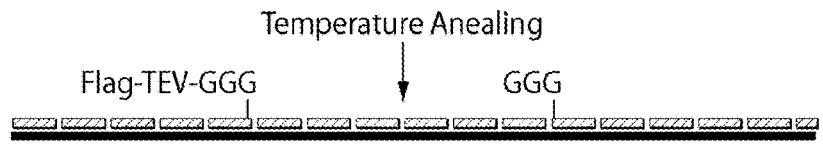
Figure 7C:
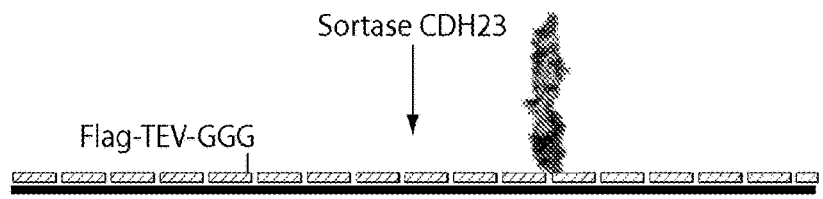
Figure 7D:
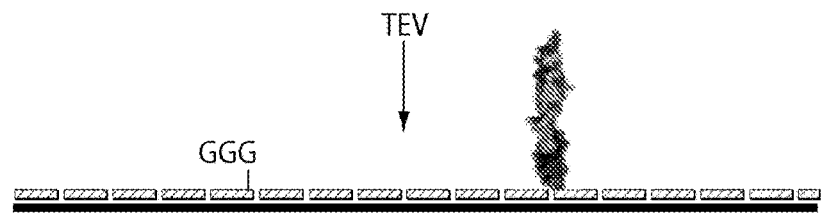
Figure 7E:
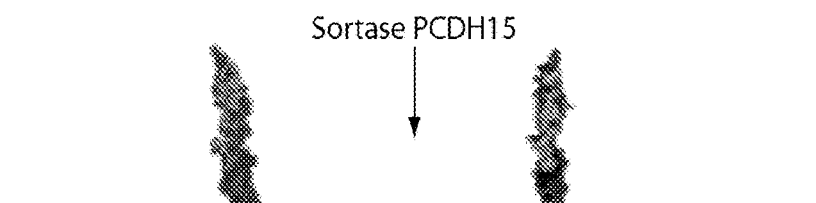
Figure 7F:
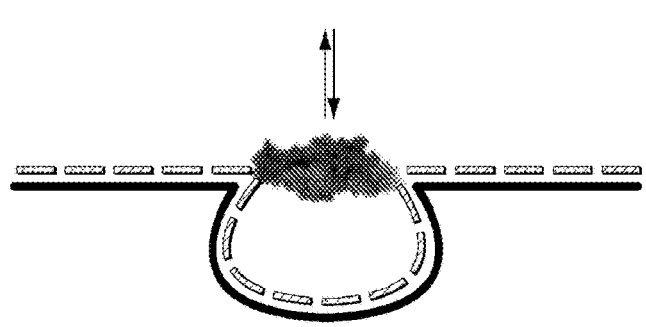

If X' is chosen to be 6-histidine residues (His-tag) (SEQ ID NO: 6), as is often the case for protein purification, then the system has a built in purification scheme. If the protein of interest, the TEV protease, and the sortase enzyme all have a His-tag, and the sortase reaction selectively cleaves the His-tag off of the final product, washing the reaction product over commercially available anti-His beads results in the supernatant containing only the desired product (FIG. 6).

The disclosure provides a complex comprising a nucleic acid covalently conjugated to a protein through an amino acid linker. The amino acid linker may have an amino acid sequence of $LPXTG_n$ (N to C order), where X is any amino acid, and n is one or more (SEQ ID NO: 17). The amino acid linker may have an amino acid sequence of $LPETG_n$ (N to C order, SEQ ID NO: 4), where n is one or more. In preferred embodiments, n is 3, and the linker has an amino acid sequence of LPETGGG (SEQ ID NO: 5). The complex has a structure as follows:

Nucleic acid-GGGTEPL-protein of interest-$NH_2$, where $NH_2$ refers to the amino terminus of the protein of interest. In other words, the protein is conjugated to the nucleic acid, through the linker, via its carboxy terminus. This is illustrated in the Figures. It will be obvious to those of ordinary skill that as illustrated, the GGGTEPL sequence is in a C to N direction (SEQ ID NO: 5). In other embodiments, the protein may be conjugated to the linker via its amino terminus.

The nucleic acid may be any length. Its length may be dictated by the ultimate use of the complex. Thus, in some instances, where shorter nucleic acids are desired, the nucleic acid may be oligonucleotides that may range in length from 1-1000, 1-500, 1-100, 1-50, or any range therebetween. The nucleic acids may be naturally occurring or non-naturally occurring. They may be prepared from a natural source, or by synthesis using for example an automated oligonucleotide synthesizer. The nucleic acids may comprise naturally occurring nucleotides or non-naturally occurring nucleotides. They may comprise naturally occurring backbone linkages or non-naturally occurring backbone linkages. The nucleic acids may comprise or consist of DNA.

The protein of interest may be virtually any protein, including naturally occurring proteins and non-naturally occurring proteins (such as for example engineered proteins). The protein may naturally contain the sortase target sequence (an example of which is $LPETG_n$ (amino to carboxy sequence) (or GnTEPL carboxy to amino sequence (SEQ ID NO: 4)). Another example is the LPETGGG sequence (SEQ ID NO: 5). The protein may be attached to the $LPXTG_n$ sequence, including the $LPETG_n$ sequence (SEQ ID NO: 17 and SEQ ID NO: 4, respectfully), including the LPETGGG (amino to carboxy) sequence (SEQ ID NO: 5)). The orientation of these sequences is shown in the Figures. This attachment can occur post-synthesis or during synthesis. The proteins may be antibodies, antibody fragments including antigen-binding antibody fragments, cell adhesion proteins such as CAM, integrins, cadherins, and the like, transcription factors, ligand receptors, ligands, signal transduction proteins, hormones, cytokines, interleukins, chemokines, and the like.

The present disclosure therefore provides a method comprising reacting a nucleic acid with a peptide comprising one or more, and preferably at least three contiguous glycine residues. In some embodiments, the nucleic acid and the peptide are reacted using a bio-orthogonal copper (I) catalyzed click chemistry reaction. In some embodiments, the nucleic acid comprises an azide and the peptide comprises an alkyne. Alternatively, the nucleic acid may comprise the alkyne and the peptide may comprise the azide. In another embodiment, a cystine containing peptide may be reacted with an amine-functionalized oligonucleotide using sulfosuccinimidyl-4-(N-maleimidomethyl) cyclohexane-1-carboxylate (SMCC). The peptide may comprise, in addition to the glycines, an purification tag and a cleavable amino acid sequence located between the purification tag and the glycines. The purification tag may be a His-tag or a Flag sequence (or Flag-tag). The cleavable amino acid sequence may be an enzyme cleavable amino acid sequence such as a TEV enzyme target sequence. The method produces a nucleic acid conjugated to the peptide, and thus the nucleic acid conjugated to at least the glycines, and optionally to the purification tag and the cleavable sequence. This conjugate may be referred to herein as a nucleic acid—peptide conjugate. The method may further comprise isolating the nucleic acid—peptide conjugate from the reaction mixture. Such isolation may comprise removal of the released Cu(I) and the uncoupled peptide and/or positive selection of the coupled oligonucleotide via the purification tag. The positive selection may be accomplished using an affinity approach such as beads, columns, slurries, and the like that comprise a binding partner for the purification tag. Such binding partners may be antibodies or antibody fragments. Once isolated, the nucleic acid—peptide conjugate may be cleaved at the cleavage sequence in order to release the purification tag. This may be accomplished by reacting the nucleic acid—peptide conjugate with an enzyme such as a TEV protease. The nucleic acid—peptide conjugate will then comprise the nucleic acid conjugated to the glycines which are now accessible to the sortase enzyme. The conjugate is then reacted with a sortase accessible protein as described below.

The present disclosure further provides a method comprising reacting (1) a nucleic acid conjugated to an amino acid sequence comprising one or more (including 3) terminal glycine (G) residues with (2) a protein conjugated to a terminal amino acid sequence of LPXTGX'$_n$, wherein X and X' are any independently selected amino acids and n is a number greater than 0 or a range of numbers greater than 0 (SEQ ID NO: 2), in the presence of a sortase enzyme to form a complex comprising the nucleic acid covalently conjugated to the protein through an amino acid linker having an amino acid sequence of LPXTGGG (N to C) or GGGTXPL (C to N) (SEQ ID NO: 9). In some embodiments, "n" is a number greater than 1.

In some embodiments, the method comprises reacting (1) a nucleic acid conjugated to an amino acid sequence comprising one or more (including 3) terminal glycine (G) residues with (2) a protein conjugated to a terminal amino acid sequence of LPETGX$_n$, wherein X is an amino acid and n is a number greater than 0 or a range of numbers greater than 0 (SEQ ID NO: 3), in the presence of a sortase enzyme to form a complex comprising the nucleic acid covalently conjugated to the protein through an amino acid linker having an amino acid sequence of LPETGGG (N to C) or GGGTEPL (C to N) (SEQ ID NO: 5). In some embodiments, "n" is a number greater than 1.

The sortase enzyme and the terminal amino acid may each comprise a purification tag such as but not limited to a His-tag.

The method may further comprise isolating the complex comprising the nucleic acid covalently conjugated to the protein. Such isolation may be accomplished by removing reaction components comprising a purification tag (preferably the same purification tag) using affinity approaches such as those described herein. Typically, any purification tag that is present in the sortase target sequence will be released once the sortase transposition occurs. Thus, the final nucleic acid—protein product will remain in the supernatant after selection for purification tags.

As described above, the nucleic acid conjugated to an amino acid sequence may be synthesized using for example a bio-orthogonal copper catalyzed click chemistry reaction as illustrated herein. The bio-orthogonal copper catalyzed click chemistry reaction forms a nucleic acid intermediate comprising a nucleic acid conjugated to one or more glycines, and optionally a cleavable sequence such as an enzyme cleavable sequence including an amino acid sequence that can be cleaved by the TEV protease (also referred to herein as TEV in some instances). The TEV cleavable sequence may be referred to herein as a TEV target sequence. The TEV target sequence may be but E-X1-X2-Y-X3-Q-(G/S), where X1, X2 and X3 represent independently selected amino acids. Cleavage occurs between the Q and G or the Q and S, typically. Examples of TEV target sequence include ENLYFQG (SEQ ID NO: 13) and ENLYFQS (SEQ ID NO: 14).

The intermediate may be reacted with an enzyme that targets the cleavable sequence. In one example, the enzyme is TEV protease. TEV protease may be conjugated to a purification sequence such as but not limited to a His-tag.

It is to be appreciated that the methods provided herein may be performed with minimal loss of reagent and thus maximum efficiency and yield. The complexes may also be obtained free of reaction components including free of substrates, intermediates, enzymes, and by-products.

The methods provided herein maintain or preserve the activity of the protein of interest through the conjugation process. In the case of enzymes or other proteins with measurable activities, the proteins maintain a specific activity that is at or near their original specific activity. Thus, the specific activity of proteins in the nucleic acid-protein complexes or conjugates are at least 75%, at least 80%, at least 85%, at least 90%, at least 95%, at least 99%, or about 100% of the specific activity of the protein in an unconjugated and unmanipulated form. Specific activity may be defined in terms of activity units per mg of protein. In the case of an enzyme, the activity unit may be referred to as an enzyme unit which is the amount of substrate converted to product per unit time under specific reaction conditions for pH and temperature.

The methods provided herein overcome various challenges and/or shortcomings of the prior art. For example, the methods provided herein do not involve suboptimal protein reaction conditions, including long incubations at room temperature, oxidizing/reducing conditions, or non-physiological pH. The methods provided herein are suitable for non-thermostable proteins that would otherwise have a tendency to aggregate and/or precipitate out of solution under the prior art conditions. In addition, by directly marking successful reactions by the simultaneous removal of an affinity label, the methods provided herein also facilitate purification of products from reactants. These methods are also versatile and robust and may be applied to virtually any protein, unlike prior art methods which tended to be optimized for individual proteins.

The disclosure further provides any of the foregoing intermediate nucleic acid-peptide complexes or final nucleic acid-protein complexes in an isolated form. An isolated form intends that the complex is physically separated from other, including in some instances all other, reaction components including substrates, intermediates, by-products, enzymes, and the like.

The present disclosure further provides a variety of compositions comprising any combination of two or more of the following:

(1) a nucleic acid conjugated to an amino acid sequence comprising a terminal glycine (G) residue such as but not limited to a GGG amino acid sequence, a GGG-TEV-Flag sequence (where "TEV" in this context refers to the TEV target sequence), or any other sequence comprising at least one glycine residue (and preferably three such residues), a cleavable sequence such as but not limited to a TEV target sequence, and a purification tag such as but not limited to a His-tag or a Flag sequence;

(2) a protein conjugated to a terminal amino acid sequence of $LPXTGX'_n$, (SEQ ID NO: 2) wherein X and X' are any independently selected amino acids and n is a number greater than 0 or a range of numbers greater than 0;

(3) a sortase enzyme; and (4) a TEV protease.

The present disclosure further provides a variety of compositions comprising any combination of two or more of the following:

(1) a nucleic acid conjugated to an amino acid sequence comprising a terminal glycine (G) residue such as but not limited to a GGG amino acid sequence, a GGG-TEV-Flag sequence (where "TEV" in this context refers to the TEV target sequence), or any other sequence comprising at least one glycine residues (and preferably three such residues), a cleavable sequence such as but not limited to a TEV target sequence, and a purification sequence such as but not limited to a tag such as a His-tag or a Flag sequence;

(2) a protein conjugated to a terminal amino acid sequence of $LPETGX_n$, wherein X is an amino acid and n is a number greater than 0 or a range of numbers greater than 0 (SEQ ID NO: 3);

(3) a sortase enzyme; and (4) a TEV protease.

In some embodiments, "n" is a number greater than 1.

Any one or any combination of the protein, the sortase enzyme, and the TEV protease may be conjugated to a purification tag such as but not limited to a His-tag or a Flag-tag. The same or different purification sequences may be used. The His-tag may be comprised in the $X'_n$ amino acid sequence that is conjugated to the protein of interest.

The composition may be in contact with beads or other affinity matrix that binds specifically to the purification tags or sequence(s). For example, the beads may be anti-His tag beads because they comprise on their surface an antibody or antibody fragment or other binding partner to the His-tag. The His-tag is an amino acid sequence comprised of contiguous histidine residues including but not limited to 6 histidine residues (SEQ ID NO: 6).

"n" as used above may be any number or any range of numbers including but not limited to from 1 to 100, or from 1 to 99, or from 1 to 90.

The disclosure further provides any of the foregoing nucleic acid-protein complexes in a composition. These compositions and any of the other compositions provided herein may further comprise a carrier such as but not limited to a pharmaceutically acceptable carrier. The term "pharmaceutically-acceptable carrier" means one or more compatible solid or liquid filler, diluents or encapsulating substances which are suitable for administration to a human or other subject contemplated by the present disclosure. The term "carrier" denotes an organic or inorganic ingredient, natural or synthetic, with which the complexes are suspended to facilitate administration. Components of the pharmaceutical compositions are commingled in a manner that precludes interaction that would substantially impair their desired pharmaceutical efficiency. The carrier may alternatively be a carrier suitable for in vitro work but not pharmaceutically acceptable.

In some embodiments, the compositions of the invention are sterile, and optionally may comprise preservative. Compositions may be kits comprising one or more vessels or containers, optionally with instructions. The compositions may be for in vivo or in vitro use.

The complexes provided herein can be used in myriad applications, including for example, measuring the kinetics of molecular interactions, and identifying molecular binding partners (from known or unknown candidates) in screening assays. Binding interaction studies may be performed using any number of methods including but not limited to gel electrophoresis, single molecule force probes such as optical tweezers, magnetic tweezers, tethered particle motion, atomic force microscope (AFM), centrifuge force microscopy (CFM), and single molecule fluorescence imaging. Applications are further described in published PCT application WO2013/067489, the entire contents of which are incorporated by reference herein.

The disclosure further provides methods of using the nucleic acid-protein complexes in one or more nanotechnology applications such as but not limited to nucleic acid nanostructures. The complexes may also be used to study binding interactions and binding affinities and strengths of protein-protein interactions. The complexes may also be used to anchor proteins to a surface.

As used herein, a "nucleic acid nanostructure" is a rationally-designed, artificial (e.g., non-naturally occurring) structure self-assembled from individual nucleic acids. Such nanostructures may be self-assembled based on sequence complementarity of component nucleic acids including oligonucleotides. "Self-assembly" refers to the ability of nucleic acids (and, in some instances, nucleic acid nanostructures) to anneal to each other, in a sequence-specific manner, in a predicted manner and without external control. In some embodiments, nucleic acid nanostructure self-assembly methods include combining nucleic acids (e.g., single-stranded nucleic acids, or oligonucleotides) in a single vessel and allowing the nucleic acids to anneal to each other, based on sequence complementarity. In some embodiments, this annealing process involves placing the nucleic acids at an elevated temperature and then reducing the temperature gradually in order to favor sequence-specific binding. Various nucleic acid nanostructures or self-assembly methods are known and described herein.

Nucleic acid nanostructures are typically nanometer-scale structures (e.g., having length scale of 1 to 1000 nanometers), although, in some instances, the terms "nucleic acid nanostructure" and "DNA nanostructure" herein may refer to micrometer-scale structures (e.g., assembled from more than one nanometer-scale or micrometer-scale structure). In some embodiments, a nucleic acid nanostructure has a length scale of 1 to 1000 nm, 1 to 900 nm, 1 to 800 nm, 1 to 700 nm, 1 to 600 nm, 1 to 500 nm, 1 to 400 nm, 1 to 300 nm, 1 to 200 nm, 1 to 100 nm or 1 to 50 nm. In some embodiments, a nucleic acid nanostructure has a length scale of greater than 1000 nm. In some embodiments, a nucleic acid nanostructure has a length scale of 1 micrometer to 2 micrometers.

In some embodiments, a nucleic acid nanostructure assembles from a plurality of different nucleic acids (e.g., single-stranded nucleic acids). For example, a nucleic acid nanostructure may assemble from at least 10, at least 20, at least 30, at least 40, at least 50, at least 60, at least 70, at least 80, at least 90 or at least 100 nucleic acids. In some embodiments, a nucleic acid nanostructure assembles from at least 100, at least 200, at least 300, at least 400, at least 500, or more, nucleic acids. The term "nucleic acid" encompasses "oligonucleotides". In the context of DNA nanostructures, in some embodiments, an oligonucleotide has a length of 10 to 20 nucleotides, 10 to 30 nucleotides, 10 to 40 nucleotides, 10 to 50 nucleotides, 10 to 60 nucleotides, 10 to 70 nucleotides, 10 to 80 nucleotides or 10 to 90 nucleotides. In some embodiments, an oligonucleotide has a length of 20 to 50, 20 to 75 or 20 to 100 nucleotides. In some embodiments, an oligonucleotide has a length of 30, 31, 32, 33, 34, 35, 36, 37, 38, 39, 40, 41, 42, 43, 44, 45, 46, 47, 48, 49 or 50 nucleotides.

Certain of these nucleic acids may be nucleic acids conjugated to, for example, three glycines, with or without the purification tag. Alternatively, certain of these nucleic acids may be nucleic acids conjugated to proteins.

In some embodiments, a nucleic acid nanostructure is assembled from single-stranded nucleic acids, double-stranded nucleic acids, or a combination of single-stranded and double-stranded nucleic acids.

Nucleic acid nanostructures may assemble, in some embodiments, from a plurality of heterogeneous nucleic acids (e.g., oligonucleotides). "Heterogeneous" nucleic acids may differ from each other with respect to nucleotide sequence. For example, in a heterogeneous plurality that includes nucleic acids A, B and C, the nucleotide sequence of nucleic acid A differs from the nucleotide sequence of nucleic acid B, which differs from the nucleotide sequence of nucleic acid C. Heterogeneous nucleic acids may also differ with respect to length and chemical compositions (e.g., isolated v. synthetic).

The fundamental principle for designing self-assembled nucleic acid nanostructures is that sequence complementarity in nucleic acid strands is encoded such that, by pairing up complementary segments, the nucleic acid strands self-organize into a predefined nanostructure under appropriate physical conditions. This technique has been described in the art. Reference can be made to for example Seeman N. C. J. Theor. Biol. 99: 237, 1982; Seeman N. C. Nature 421: 427, 2003; Shih W. M. et al. Curr. Opin. Struct. Biol. 20: 276, 2010. This technique has been used to make a variety of structures. Such structures include without limitation lattices (see, e.g., Winfree E. et al. Nature 394: 539, 1998; Yan H. et al. Science 301: 1882, 2003; Yan H. et al. Proc. Natl. Acad. of Sci. USA 100; 8103, 2003; Liu D. et al. J. Am. Chem. Soc. 126: 2324, 2004; Rothemund P. W. K. et al. PLoS Biology 2: 2041, 2004), ribbons (see, e.g., Park S. H. et al. Nano Lett. 5: 729, 2005; Yin P. et al. Science 321: 824, 2008), tubes (see, e.g., Yan H. Science, 2003; P. Yin, 2008), finite two-dimensional and three dimensional objects with defined shapes (see, e.g., Chen J. et al. Nature 350: 631, 1991; Rothemund P. W. K., Nature, 2006; He Y. et al. Nature 452: 198, 2008; Ke Y. et al. Nano. Lett. 9: 2445, 2009; Douglas S. M. et al. Nature 459: 414, 2009; Dietz H. et al. Science 325: 725, 2009; Andersen E. S. et al. Nature 459: 73, 2009; Liedl T. et al. Nature Nanotech. 5: 520, 2010; Han D. et al. Science 332: 342, 2011), and macroscopic crystals (see, e.g., Meng J. P. et al. Nature 461: 74, 2009). All of these teachings are incorporated by reference herein.

In some embodiments, a nucleic acid nanostructure is assembled using a nucleic acid (e.g., DNA) origami approach. With a DNA origami approach, for example, a long "scaffold" nucleic acid strand is folded to a predesigned shape through interactions with relatively shorter "staple" strands. Thus, in some embodiments, a single-stranded nucleic acid for assembly of a nucleic acid nanostructure has a length of at least 500 base pairs, at least 1 kilobase, at least 2 kilobases, at least 3 kilobases, at least 4 kilobases, at least 5 kilobases, at least 6 kilobases, at least 7 kilobases, at least 8 kilobases, at least 9 kilobases, or at least 10 kilobases. In some embodiments, a single-stranded nucleic acid for assembly of a nucleic acid nanostructure has a length of 500 base pairs to 10 kilobases, or more. In some embodiments, a single-stranded nucleic acid for assembly of a nucleic acid nanostructure has a length of 7 to 8 kilobases. In some embodiments, a single-stranded nucleic acid for assembly of a nucleic acid nanostructure comprises the M13 viral genome.

In some embodiments, a nucleic acid nanostructure is assembled from single-stranded tiles (SSTs) (see, e.g., Wei B. et al. Nature 485: 626, 2012) or nucleic acid "bricks" (see, e.g., Ke Y. et al. Science 388:1177, 2012; International Publication Number WO 2014/018675 A1, published Jan. 30, 2014). For example, single-stranded 2- or 4-domain oligonucleotides self-assemble, through sequence-specific annealing, into two- and/or three-dimensional nanostructures in a predetermined (e.g., predicted) manner. As a result, the position of each oligonucleotide in the nanostructure is known. In this way, a nucleic acid nanostructure may be modified, for example, by adding, removing or replacing oligonucleotides at particular positions. The nanostructure may also be modified, for example, by attachment of moieties, at particular positions. This may be accomplished by using a modified oligonucleotide as a starting material or by modifying a particular oligonucleotide after the nanostructure is formed. Therefore, knowing the position of each of the starting oligonucleotides in the resultant nanostructure provides addressability to the nanostructure.

The nanostructure may also be modified by placing in a controlled and directed manner proteins of one or more types using the nucleic acid conjugates of this disclosure.

Some aspects of the present disclosure are directed to assembling nucleic acid nanostructures using annealing processes. In some embodiments, nucleic acids are combined, in a single vessel such as, but not limited to, a tube, a well or a vial. The molar amounts of nucleic acids that are used may depend on the frequency of each nucleic acid in the nanostructure desired and the amount of nanostructure desired. In some embodiments, the nucleic acids may be present in equimolar concentrations. In some embodiments, each nucleic acid (e.g., oligonucleotide) may be present at a concentration of about 200 nM. In some embodiments, the nucleic acids are placed in a solution. The solution may be buffered, although the annealing reaction can also occur in the absence of buffer. The solution may further comprise divalent cations such as, but not limited, to $Mg^{2+}$. The cation or salt concentration may vary. An exemplary concentration is about 490 mM. The solution may also comprise EDTA or other nuclease inhibitors in order to prevent degradation of the nucleic acids.

An annealing reaction is carried out, in some embodiments, by heating the solution containing nucleic acids and then allowing the solution to slowly cool down (e.g., heated and then placed in a room temperature environment). The temperature of the reaction should be sufficiently high to melt any undesirable secondary structure such as hairpin structures and to ensure that the nucleic acids are not bound incorrectly to other non-complementary nucleic acids. The temperature, therefore, may be initially raised to any temperature below or equal to 100° C. For example, the temperature may be initially raised to 100° C., 95° C., 90° C., 85° C., 80° C., 75° C., 70° C., 65° C. or 60° C. The temperature may be raised by placing the vessel in a hot water bath, heating block or a device capable of temperature control, such as a thermal cycler (e.g., polymerase chain reaction (PCR) machine). The vessel may be kept in that environment for seconds or minutes. In some embodiments, an incubation time of about 1-10 minutes is sufficient.

Once nucleic acid incubation at an elevated temperature is complete, the temperature may be dropped in a number of ways. The temperature may be dropped, for example, in an automated manner using a computer algorithm that drops the temperature by a certain amount and maintains that temperature for a certain period of time before dropping the temperature again. Such automated methods may involve dropping the temperature by a degree in each step or by a number of degrees at each step. The vessel may thus be heated and cooled in the same device. As another example, the heated solution may be placed at room temperature to cool. An exemplary process for dropping temperature is as follows. To effect a drop in temperature from about 80° C. to about 24° C., the temperature is changed from 80° C. to 61° C. in one degree increments at a rate of 3 minutes per degree (e.g., 80° C. for 3 minutes, 79° C. for 3 minutes, etc.). The temperature is then changed from 60° C. to 24° C. in one degree increments and at a rate of about 120 minutes per degree (e.g., 60° C. for 120 minutes, 59° C. for 210 minutes, etc.). The total annealing time for this process is about 17 hours. In accordance with the present disclosure, under these conditions, nucleic acids (e.g., oligonucleotides) self-assemble into a nanostructure of predetermined and desired shape and size.

An example of a specific annealing process uses one hundred different 200 nM oligonucleotides in solution (e.g., 5 mM Tris-1 mM EDTA (TE), 40 mM MgCl2) and the solution is heated to about 90° C. and then cooled to about 24° C. over a period of about 73 hours, as described above with a 3 minute per degree drop between 80° C. and 61° C., and a 120 minute per degree drop between 60° C. and 24° C. It should be understood that the foregoing annealing process is exemplary and that other annealing processes may be used in accordance with the present disclosure.

Nucleic acids of the present disclosure include DNA such as D-form DNA and L-form DNA and RNA, as well as various modifications thereof. Nucleic acid modifications include base modifications, sugar modifications, and backbone modifications. Non-limiting examples of such modifications are provided below.

Examples of modified DNA nucleic acids (e.g., DNA variants) that may be used in accordance with the present disclosure include, without limitation, L-DNA (the backbone enantiomer of DNA, known in the literature), locked nucleic acid (LNA), and co-nucleic acids of the above such as DNA-LNA co-nucleic acids. Thus, the present disclosure contemplates nanostructures that comprise DNA, RNA, LNA, or combinations thereof. It is to be understood that the nucleic acids used in methods and compositions of the present disclosure may be homogeneous or heterogeneous in nature. As an example, nucleic acids may be completely DNA in nature or they may be comprised of DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some embodiments, nucleic acids are nuclease-resistant.

Nucleic acids of the present disclosure, in some embodiments, have a homogenous backbone (e.g., entirely phosphodiester or entirely phosphorothioate) or a heterogeneous (or chimeric) backbone. Phosphorothioate backbone modifications may render an oligonucleotide less susceptible to nucleases and thus more stable (as compared to a native phosphodiester backbone nucleic acid) under certain conditions. Other linkages that may provide more stability to a nucleic acid of the present disclosure include, without limitation, phosphorodithioate linkages, methylphosphonate linkages, methylphosphorothioate linkages, boranophosphonate linkages, peptide linkages, alkyl linkages and dephospho-type linkages. Thus, in some embodiments, nucleic acids have non-naturally occurring backbones.

In some embodiments, nucleic acids of the present disclosure do not encode a product (e.g., a protein).

Nucleic acids of the present disclosure, in some embodiments, additionally or alternatively comprise modifications in their sugars. For example, a β-ribose unit or a β-D-2'-deoxyribose unit can be replaced by a modified sugar unit, wherein the modified sugar unit is, for example, selected from b-D-ribose, a-D-2'-deoxyribose, L-2'-deoxyribose, 2'-F-2'-deoxyribose, arabinose, 2'-F-arabinose, 2'-O—(C1-C6)alkyl-ribose, preferably 2'-O—(C1-C6)alkyl-ribose is 2'-O-methylribose, 2'-O—(C2-C6)alkenyl-ribose, 2'-[O—(C1-C6)alkyl-O—C1-C6)alkyl]-ribose, 2'-NH2-2'-deoxyribose, b-D-xylo-furanose, a-arabinofuranose, 2,4-dideoxy-b-D-erythro-hexo-pyranose, and carbocyclic (see, e.g., Froehler J. Am. Chem. Soc. 114:8320, 1992, incorporated by reference herein) and/or open-chain sugar analogs (see, e.g., Vandendriessche et al. Tetrahedron 49:7223, 1993, incorporated by reference herein) and/or bicyclosugar analogs (see, e.g., Tarkov M. et al. Hely. Chim. Acta. 76:481, 1993, incorporated by reference herein).

Nucleic acids of the present disclosure, in some embodiments, comprise modifications in their bases. Modified bases include, without limitation, modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Nucleic acids of the present disclosure, in some embodiments, are synthesized in vitro. Thus, in some embodiments, nucleic acids are synthetic (e.g., not naturally-occurring). Methods for synthesizing nucleic acids, including automated nucleic acid synthesis, are known. For example, nucleic acids having modified backbones, such as backbones comprising phosphorothioate linkages, and including those comprising chimeric modified backbones, may be synthesized using automated techniques employing either phosphoramidate or H-phosphonate chemistries (see, e.g., F. E. Eckstein, "Oligonucleotides and Analogues—A Practical Approach" IRL Press, Oxford, UK, 1991; and Matteucci M. D. et al. Tetrahedron Lett. 21: 719, 1980). Synthesis of nucleic acids with aryl- and alkyl-phosphonate linkages are also contemplated (see, e.g., U.S. Pat. No. 4,469,863). In some embodiments, nucleic acids with alkylphosphotriester linkages (in which the charged oxygen moiety is alkylated, e.g., as described in U.S. Pat. No. 5,023,243 and European Patent No. 092,574) are prepared by automated solid phase synthesis using commercially available reagents. Methods for making other DNA backbone modifications and substitutions have been described (see, e.g., Uhlmann E. et al. Chem. Rev. 90:544, 1990; Goodchild J. Bioconjugate Chem. 1:165, 1990; Crooke S. T. et al. Annu. Rev. Pharmacol. Toxicol. 36:107, 1996; and Hunziker J. et al. Mod Synth Methods 7:331, 1995, each of which is incorporated by reference) and may be used in accordance with the present disclosure.

Various exemplary embodiments of the disclosure are described in greater detail in the following Examples.

EXAMPLES

Methods

Four protocols are presented describing:

2.1) the formation of a DNA-oligonucleotide bearing a sortase-compatible GGG-peptide, 2.2) the sortase-catalyzed coupling of a protein to the DNA-peptide chimera, and 2.3/2.4) the integration of DNA-protein hybrids into self-assembling nanostructures for thermostable/non-thermostable proteins.

The oligonucleotides functionalized for these experiments were both 60 base pairs (bp) oligonucleotides referred to as "oligo 1" and "oligo 2". Oligo 1 was synthesized with a 3'-azide and oligo 2 was synthesized with a 5'-azide, and both were commercially available from IDT, a custom oligonucleotide manufacturer. The peptide used in these experiments has the sequence of (amino to carboxy or N to C) Flag-TEV-GGG-Pra (i.e., DYKDDDDK-ENLYFQ-GGG-Pra), where "Pra" is the unnatural amino acid propargylglycine (SEQ ID NO: 12). Such synthetic peptides may be ordered from commercial sources such as NeoBioLab. The Pra residue provides an alkyne, the complimentary click reagent. Additionally, to facilitate purification, a Flag-tag was added to the N-terminus of the peptide (denoted "Flag" in the sequence). As the sortase enzyme requires the GGG to be on a free N-terminus, a tobacco etch virus cleavage site (TEV) was inserted to allow for removal of the Flag-tag.

2.1 Protocol for the Formation of Oligonucleotides with Sortase-Compatible GGG Peptide 2.1.1 Preparation of Reagents a. Solubilize the peptide to 1 mg/ml (0.5 mM) in nuclease-free water. The propargylglycine reduces solubility of the peptide and a small amount of ammonium bicarbonate can be added to solubilize the peptide.

b. Solubilize the oligonucleotide at 100 µM in nuclease-free water.

c. Prepare a 94.2 g/L (59 mM) aqueous $CuSO_4$ stock. Anhydrous $CuSO_4$ is preferred.

d. Prepare a 264.2 g/L (0.21M) aqueous ascorbic acid stock. The ascorbic acid serves to reduce the Cu(II) (blue) to the catalytically active Cu(I) (green).

2.1.2 Click-Coupling of the Peptide to the Oligonucleotide (FIG. 1)

a. Combine the following in a 250 uL DNA-low-bind tube
            i. 35 µL of the azide-oligo
            ii. 30 µL or the peptide
            iii. 12 µL of the ascorbic acid
                1. $CO_2$ (gas) is produced from the ammonium bicarbonate
                2. Although the peptide is insoluble at neutral pH, it is soluble under both the slightly basic ammonium bicarbonate conditions and the acidic ascorbic acid conditions
            iv. 8.5 µL of the $CuSO_4$.
        b. Allow the reaction to sit for 2 hours at room temperature to ensure completion.
        c. Some of the Cu will be reduced to Cu(0) metal, which will precipitate out.

2.1.3 Purification of the Peptide-Oligonucleotide Chimera a. Removal of Uncoupled Peptide (Either Method 1 or Method 2 can be Used)
        Method 1: Neutralization
            1. Neutralizing the solution via the addition of 250 µL of TBS (50 mM TrisHCl, 300 mM NaCl pH 7.6) will cause uncoupled peptide to precipitate.
            2. The copper metal and precipitated peptide can be pelleted by centrifugation at 16,000 g for 5 min. The supernatant will contain coupled and uncoupled oligonucleotide and excess Cu(I) can be dialyzed out using a 6-8 kDa membrane (Mini GeBAflex-tube, T070-6).
        Method 2: QiaQuick Nucleotide Removal Kit (Qiagen)
            1. Following the kit protocol will remove the copper metal, Cu(I), Cu(II), and the uncoupled peptide.
            2. The protocol should be followed as instructed by the manufacturer, but the wash step should be repeated a second time.
            3. Perform the elution with 200 µL of TBS.

2.1.4 Removal of Uncoupled Oligonucleotide (FIG. 3)

a. Wash 1 ml of Anti-Flag M2 magnetic beads (Sigma-Aldrich, M8823) three times with 1 ml of TBS.
        b. Apply the product of the Qiagen purification column and allow to bind for 1-2 hrs rotating at room temperature.
        c. Wash the beads at least 4 times with 500 µl of TBS being sure to agitate the beads to remove any uncoupled oligo. A wide boar pipette may be preferable when agitating the beads.
        d. Elute with 1 ml of 0.1 mg/ml (Sigma) Flag peptide in eTBS (50 mM TrisHCl, 150 mM NaCl). Allow 1 hour rotating at room temperature for elution.
        e. A second elution can be performed, but >85% will be recovered in the first elution.

2.1.5 TEV-Cleavage of the Flag-tag (FIG. 4)

a. Add 2 µL of 2 mg/ml TEV protease (Sigma-Aldrich, T4455) to each ml of eluted product.
        b. Incubate in a 30° C. water bath overnight.
        c. Running a 4-20% gradient poly-acrylamide gel with the binding, wash, and elution (cleaved and uncleaved) supernatants reveals that the product has been successfully purified of uncoupled oligonucleotide (the 60 bp band is eliminated with successive washes) and cleaved (after cleavage the band shifts back near 60 bp).

Figure 8:
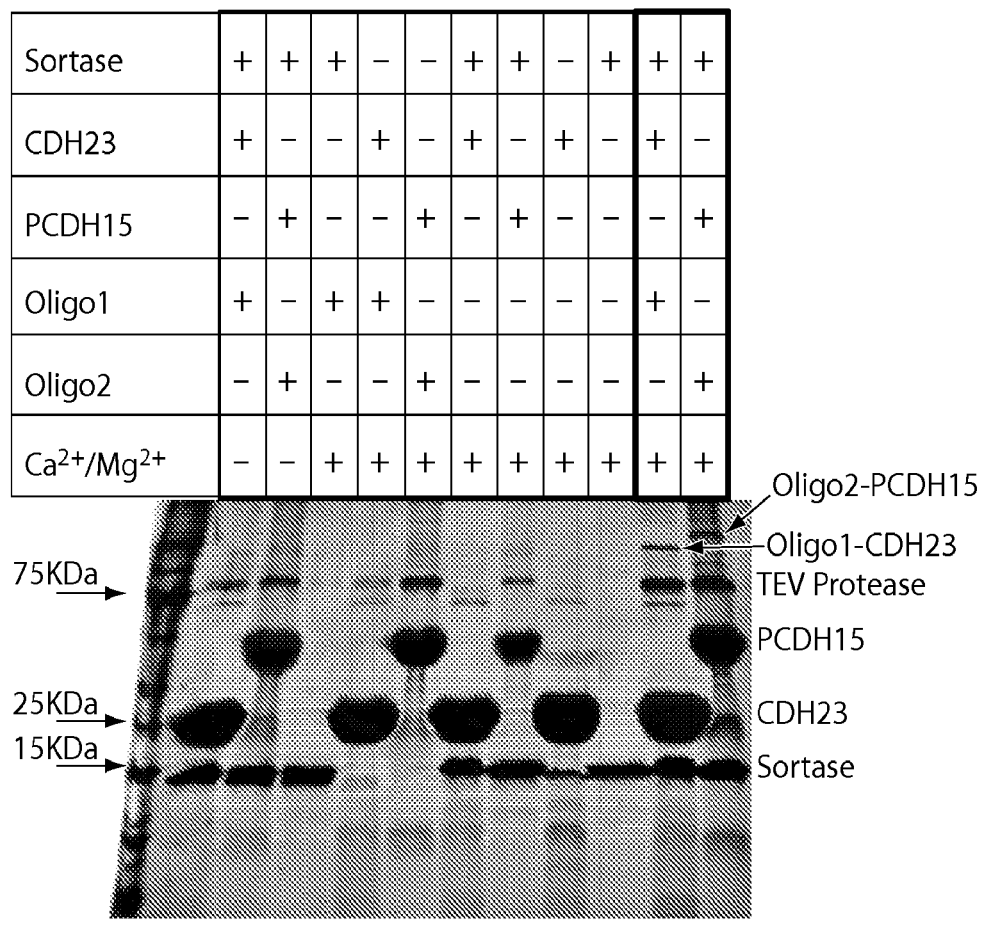
FIG. 8. SDS-PAGE verification of protein-DNA coupling. Successful coupling in this experiment required the presence of a protein comprising the LPETG sequence (SEQ ID NO: 4), a GGG-oligo, the sortase enzyme, and divalent cations (primarily $Ca^{2+}$). Only when all the requisite constituents are present (last two columns of the grid), were coupled products detectable.

2.1.6 The final product will herein be referred to as GGG-oligo.
  a. While not necessary, the TEV protease and cleaved peptide can be removed by repeating the Qiagen nucleotide removal kit as described above. This step has not proven to be necessary 2.2 Protocol for Sortase Coupling LPETG-Tagged Proteins to GGG-Oligonucleotides 2.2.1 Preparation of Reagents
  a. The GGG-oligonucleotide at a concentration of ~2 µM, as judged by band intensity on the polyacrylamide gel.
    i. Gel was stained with SYBR-Gold (Invitrogen, S11494), imaged using a GE Typhoon FLA-9500, and analyzed using ImageJ (NIH, 1.46r)
  b. Two proteins, proteins 1 and 2, are coupled to two different oligos, oligos1 and 2
    i. In this example protein 1 is CDH23 and protein 2 is PCDH15, both produced as described in (Sotomayor et al., Nature, 492:128-132, 2012; Sotomayor et al., Neuron, 66: 85-100, 2010).
  c. Proteins may be used at a minimum concentration of 0.1 mM.
    i. CDH23 and PCDH15 stocks were at 2.5 and 2.7 mg/ml respectively in TBS+5 mM $CaCl_2$ (~0.1 mM)
      1. CDH23-LPETG (SEQ ID NO: 4) was a fragment containing two extracellular domains used in a crystallographic study (Sotomayor et al., Nature, 492:128-132, 2012). The protein was modified by appending LPETG (SEQ ID NO: 4) between the His-tag and the C-terminus of the protein
      2. PCDH15-LPETG (SEQ ID NO: 4) was a fragment containing two extracellular domains used in a crystallographic study (Sotomayor et al., Nature, 492:128-132, 2012). The protein was modified by appending LPETG (SEQ ID NO: 4) between the His-tag and the C-terminus of the protein
  d. Sortase stock was at 1.5 mg/ml in TBS+10%-glycerol
    i. An evolved variant of sortase (Chen et al., PNAS 108:11399-11404, 2011) was used
  e. Sortase Reaction buffer consisted of the following:
    i. 300 mM TrisHCl pH7.5
    ii. 5 mM $MgCl_2$
    iii. 5 mM $CaCl_2$
    iv. 150 mM NaCl 2.2.2 Sortase Coupling of Protein 1 to oligo 1 (FIG. 5)
  a. Mix the following in a 250 µL mini GEBAflex-tube
    i. 140 µL of 2 µM GGG-oligo1
    ii. 40 µL of 0.1 mM protein1-LPETG-HHHHHH (SEQ ID NO: 15)
      1. The protein is added in large excess to drive coupling to completion with respect to the oligo
    iii. 5 µL of Sortase
    iv. 65 µL of Sortase Rxn Buffer
  b. Place the GEBA Flex tube in 1 L of Sortase RXN buffer and allow the reaction to go for 1 hr at RT or 4-5 hours at 4° C.
    i. The dialysis column will allow any Flag Peptide to dialyze out and will remove the sortase reaction byproduct, G-HHHHHH (SEQ ID NO: 16), which can compete with the Oligo
  c. FIG. 8 shows SDS-PAGE analysis indicating that the protein-oligonucleotide chimera is only formed when all components are present 2.2.3 Purification of Protein-Oligonucleotide Chimera (FIG. 6)
  a. The TEV, sortase, protein 1, and protein 2 all bear His-tags. The sortase reaction, however, selectively cleaves the His-tag off of the final product. Thus passing the product over anti-His magnetic beads will remove these reactants leaving the final product in the supernatant.
    i. Anti-His beads may be preferred in some instances instead of Ni-NTA. The Ni-NTA beads in some instances tend to bind the oligos quite strongly and very high salt may be required to remove them.
  b. Wash 1 ml of magnetic Anti-His beads (GenScript, L00275) 2 times with 1 ml of TBS
    i. This is to remove any phosphate from the storage solution to prevent calcium-phosphate crystal formation. Omitting this step may result in large losses in latter steps
  c. Wash 3 more times with 1 ml of TBS+5 mM $CaCl_2$
  d. Apply the product of the sortase reaction and allow 2 hours rotating at 4° C. for binding
  e. The supernatant contains the DNA-protein hybrid free of any other proteins 2.3 Protocol for Hybridization of DNA Protein Hybrid to Scaffold (Thermostable Proteins)

If the protein of interest can withstand being heated to 40° C., the oligos can be hybridized to the scaffold, in this case linearized M13 (Halvorsen et al., Nanotechnol. 22:494005-494012, 2011), by adding the oligos in a one-to-one ratio to the scaffold, then ramping from 40° C. to 20° C. at half a degree per minute in a thermocycler (Halvorsen et al., Nanotechnol. 22:494005-494012, 2011).

One can anneal all unfunctionalized oligos from 95° C. in 0.5 degree steps to 20° C. The functionalized oligos can be added during this run by pausing the thermocycler once it reaches 40° C., adding the functionalized oligos. If the protein is not thermostable, an alternate approach can be taken as described below in section 2.4.

2.4 Protocol for Hybridization of DNA-Protein Hybrid to Scaffold (Non-Thermostable Proteins)

In this example the CDH23 and PCDH15 fragments are not very thermostable and hybridization through temperature annealing was not an option. For this system the GGG-oligos were hybridized onto the scaffold and the sortase coupling was done in situ directly on the scaffold. Performing the coupling on the oligos before hybridization allows one to easily control which protein is attached to which oligo. For this system selective coupling was achieved using the Flag-tag as a protecting group. That is, oligo 1 was processed fully, resulting in a GGG-oligo, while oligo 2 did not undergo TEV cleavage of its Flag-tag.

An additional concern is ensuring that each site on the scaffold receives its complimentary oligo. To accomplish this, the oligos are added at 50-fold excess. This, however, results in a large surplus of free floating oligos. This can be a problem if there is an excess of GGG-oligonucleotide floating around which will compete with the in situ reaction. To overcome this issue excess oligos had to be removed from the solution.

2.4.1 Preparation of Reagents
  a. The GGG- and Flag-TEV-GGG-oligos should be concentrated to ~10 µM
    i. This can be achieved by using a speedvac (Thermo-Savant, SC210A) or a 3 kDa spin column (Vivaspin 500, VS0191). If a speedvac is used, the oligos should first be dialyzed into water to remove salts before concentration.

2.4.2 Annealing oligos
a. Mix the following in a low-bind 250 µL PCR tube
   ii. 5 µL of 20 nM origami scaffold (linear M13, in this case)
   iii. 1.19 µL of 100 nM mixture (equal parts) of all unfunctionalized oligos
   iv. 0.5 µL of 10 nM GGG-oligo 1
   v. 0.5 µL of 10 nM Flag-TEV-GGG-oligo 2
b. Subject the mixture to a temperature ramp from 95° C. to 20° C. at 0.5 degree increments to anneal the oligos to the scaffold.

2.4.3 Removal of excess oligos by PEG-precipitation (modified from Hartley and Bowen, Focus, 66: 27-28, 1996)
a. Dilute the product of the annealing in 115 µL of 4%, by weight, 8K PEG (Amresco, 0159) in 30 mM $MgCl_2$
b. Mix thoroughly
c. Centrifuge at 16,000 g for 30 min at 25° C.
d. Remove the top 112 µL leaving the bottom 10 µL which should contain the precipitated scaffold
e. Dilute the remaining 10 µL with another 115 µL of 4%, by weight, 8K PEG (Amresco, 0159) in 30 mM $MgCl_2$
   i. Be sure to mix thoroughly.
f. Centrifuge at 16,000 g for 30 min at 25° C.
g. Remove the top 115 µL of supernatant
h. The remaining 10 µL should have the scaffold free of any detectable amount of unhybridized oligo 2.4.4.1 In situ coupling of protein 1-LPETG-HHHHHH (SEQ ID NO: 15) to the GGG-Oligo
a. Mix the following
   i. 40 µL 1M Tris HClpH 7.5
   ii. 0.8 µL 1M $CaCl_2$
   iii. 8 µL 3M NaCl
   iv. 10 µL of PEG-precipitated scaffold
   v. 50 µL of 14 mg/ml sortase
   vi. 15 µL of 0.1M protein1-LPETG-HHHHHH (SEQ ID NO: 15)
b. Place the mixture into a dialysis membrane (Spectra/Por MicroFloat-a-lyzer, F235053)
c. Place the Floatalyzer in 1 L of sortase reaction buffer
d. Allow this reaction to run for 0.5-1 hr at RT before moving to 4° C. for an additional 2 hours (upon transferring to 4° C. it is best to transfer to a pre-chilled liter of sortase reaction buffer)
e. Add 4 µL of 2 mg/ml TEV and allow to sit at room temperature for 1 hr
f. Wash 1 ml of magnetic Anti-His beads (GenScript, L00275) 2 times with 1 ml of TBS. This is to remove any phosphate from the storage solution to prevent calcium-phosphate crystal formation. Omitting this step may result in large losses in latter steps.
g. Wash 3 more times with 1 ml of TBS+5 mM $CaCl_2$
h. Apply the product of the sortase reaction and allow 2 hours rotating at 4° C. for binding
i. The supernatant contains the DNA-protein hybrid. Free of TEV and excess CDH23
j. Add the following to the supernatant and place in a new Floatalyzer
   vii. 15 µL of 0.1M protein2-LPETG-HHHHHH (SEQ ID NO: 15)
   viii. 50 µL of 14 mg/ml sortase
k. Repeat Steps b, c, d, f, g, and h
l. The supernatant contains the pure site-directedly bi-functionalized DNA-protein hybrid.
m. Functionality of the nanoswitch was assayed by gel electrophoresis as previously described in (Halvorsen et al., Nanotechnol. 22:494005-494012, 2011).

Conclusions

This disclosure has provided detailed protocols for reliably linking proteins to DNA-oligos, while preserving protein function. Additionally, methods are provided for the incorporation of these chimeras into self-assembling nanostructures. These techniques frontload all harsh chemistries to synthetic oligos and peptides, which are more amenable to these non-physiological conditions. The use of click chemistry ensures that linkages are bio-orthogonal, site directed, and efficient. The use of an evolved sortase allows for protein coupling to occur under conditions favorable for protein stability. The protocols have been designed to be resilient to changes in the protein of interest, and all materials are commercially available. The built in purification schemes allow for fast and efficient purification, allowing for the immediate use of the chimeric product. When combined with a library of sortase compatible oligos and peptides, this flexible and modular approach could enable the creation of a wide range of functional nanostructures on demand. Furthermore, this approach expands the range of functional DNA-protein chimeras that can be constructed, enabling the incorporation of previously inaccessible protein machinery to generate nanostructures with previously unobtainable functionalities.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising
reacting a nucleic acid conjugated to an amino acid sequence comprising a terminal glycine (G) residue with a protein comprising a terminal amino acid sequence of LPXTGX'$_n$ (SEQ ID NO: 2), wherein X is any amino acid, X'$_n$ is a string of independently selected amino acids of length n, and n is a number or any range of numbers from 1 to 100, in the presence of a sortase enzyme to form a complex comprising the nucleic acid covalently conjugated to the protein through an amino acid linker having an amino acid sequence of LPXTGGG (SEQ ID NO: 9), wherein X is any amino acid, wherein the nucleic acid conjugated to an amino acid sequence is incorporated in a nucleic acid nanostructure.

2. The method of claim 1, wherein the sortase enzyme and the protein comprising a terminal amino acid sequence of LPXTGX'$_n$ (SEQ ID NO: 2) each comprises a His-tag.

3. The method of claim 1, wherein the terminal amino acid sequence is LPETGX'$_n$ (SEQ ID NO: 3), wherein X'$_n$ is a string of amino acids of length n and n is a number or any range of numbers from 1 to 100, and wherein the amino acid sequence of the amino acid linker is LPETGGG (SEQ ID NO: 5).

4. The method of claim 1, wherein n is a number greater than 1, and less than or equal to 100.

5. The method of claim 1, wherein the nucleic acid conjugated to an amino acid sequence comprising a terminal glycine (G) residue is formed by a bio-orthogonal copper catalyzed click chemistry reaction.

6. The method of claim 5, wherein the bio-orthogonal copper catalyzed click chemistry reaction forms a nucleic acid intermediate comprising a nucleic acid conjugated to one or more glycine (G) residues and a TEV target amino acid sequence.

7. The method of claim 6, wherein the nucleic acid intermediate is reacted with TEV protease.

8. The method of claim 7, wherein the TEV protease is conjugated to a His-tag.

9. The method of claim 2, wherein the His-tag is an amino acid sequence of six histidine residues (SEQ ID NO: 6).

10. The method of claim 1, the protein in the formed complex has a specific activity that is at least 75% of the specific activity of the protein in an unconjugated and unmanipulated form.

11. The method of claim 1, the protein in the formed complex has a specific activity that is at least 80% of the specific activity of the protein in an unconjugated and unmanipulated form.

12. The method of claim 1, the protein in the formed complex has a specific activity that is at least 90% of the specific activity of the protein in an unconjugated and unmanipulated form.

13. The method of claim 1, the protein in the formed complex has a specific activity that is about 100% of the specific activity of the protein in an unconjugated and unmanipulated form.

* * * * *

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

Glu Asn Leu Tyr Phe Gln
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Leu Pro Xaa Thr Gly Xaa
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 3

Leu Pro Glu Thr Gly Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Leu Pro Glu Thr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Leu Pro Glu Thr Gly Gly Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 6

His His His His His His
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Asp Tyr Lys Asp Asp Asp Asp Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 8

Leu Pro Xaa Thr Gly Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 9

Leu Pro Xaa Thr Gly Gly Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Leu Pro Glu Thr Gly Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 11

Leu Pro Glu Thr Gly Gly Gly
1               5

<210> SEQ ID NO 12
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (18)..(18)
<223> OTHER INFORMATION: Xaa is propargylglycine

<400> SEQUENCE: 12

Asp Tyr Lys Asp Asp Asp Asp Lys Glu Asn Leu Tyr Phe Gln Gly Gly
1               5                   10                  15

Gly Xaa
```

```
<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 13

Glu Asn Leu Tyr Phe Gln Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 14

Glu Asn Leu Tyr Phe Gln Ser
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 15

Leu Pro Glu Thr Gly His His His His His His
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 16

Gly His His His His His His
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Leu Pro Xaa Thr Gly
1               5
```